(12) United States Patent
Yang et al.

(10) Patent No.: US 9,701,669 B2
(45) Date of Patent: Jul. 11, 2017

(54) PREPARATION AND USE OF 7A-AMIDE SUBSTITUTED- 6,6-DIFLUORO BICYCLIC HIMBACINE DERIVATIVES AS PAR-1 RECEPTOR ANTAGONISTS

(71) Applicant: Merck Sharp & Dohme Corp., Rahway, NJ (US)

(72) Inventors: Zhiqiang Yang, Westfield, NJ (US); Fengqi Zhang, Edison, NJ (US); Guizhen Dong, Dayton, NJ (US); Sandra Lee Knowles, Princeton, NJ (US); Milana Maletic, Summit, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/912,233

(22) PCT Filed: Aug. 18, 2014

(86) PCT No.: PCT/US2014/051416
§ 371 (c)(1),
(2) Date: Feb. 16, 2016

(87) PCT Pub. No.: WO2015/026693
PCT Pub. Date: Feb. 26, 2015

(65) Prior Publication Data
US 2016/0185764 A1   Jun. 30, 2016

Related U.S. Application Data

(60) Provisional application No. 61/868,609, filed on Aug. 22, 2013.

(51) Int. Cl.
| | | |
|---|---|---|
| *A61K 31/4427* | (2006.01) | |
| *C07D 405/06* | (2006.01) | |
| *C07D 405/14* | (2006.01) | |
| *A61K 45/06* | (2006.01) | |
| *A61K 31/4365* | (2006.01) | |
| *A61K 31/443* | (2006.01) | |
| *A61K 31/444* | (2006.01) | |
| *A61K 31/616* | (2006.01) | |

(52) U.S. Cl.
CPC ........ *C07D 405/14* (2013.01); *A61K 31/4365* (2013.01); *A61K 31/443* (2013.01); *A61K 31/444* (2013.01); *A61K 31/616* (2013.01); *A61K 45/06* (2013.01); *C07D 405/06* (2013.01)

(58) Field of Classification Search
CPC ............................ C07D 405/06; C07D 405/14
See application file for complete search history.

(56) References Cited

U.S. PATENT DOCUMENTS 6,326,380 B1   12/2001   Chackalamannil et al.
7,776,889 B2   8/2010   Chackalamannil et al.
(Continued)

FOREIGN PATENT DOCUMENTS

KR   20120111887   10/2012
WO   WO2011162562   12/2011
(Continued)

OTHER PUBLICATIONS

International Search Report and Written Opinion for PCT/US2014/051416 mailed Nov. 28, 2014, 9 pages.
(Continued)

*Primary Examiner* — Brian McDowell
(74) *Attorney, Agent, or Firm* — Nicole M. Beeler; Catherine D. Fitch

(57) ABSTRACT

The present invention relates to bicyclic himbacine derivatives of the formula

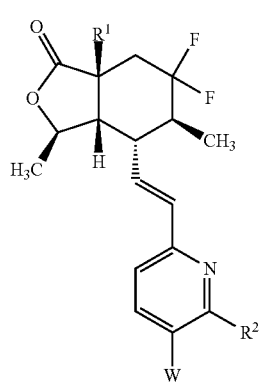

I or a pharmaceutically acceptable salt thereof
wherein:
$R^1$ is $-[C(R^a)(R^b)]_x-[C(R^b)(R^b)]_y-C(O)NH_2$, or $-N(H)-[(CH_2)]_z-C(O)-NH_2$,
W is

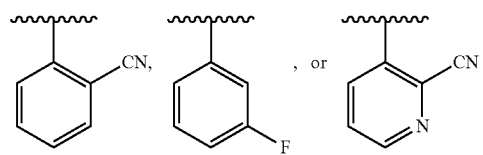

and the remaining variables are described herein. The compounds of the invention are effective inhibitors of the PAR-1 receptor. The inventive compounds may be used for the
(Continued)

treatment or prophylaxis of disease states such as ASC, secondary prevention of myocardial infarction or stroke, or PAD.

13 Claims, No Drawings

(56) References Cited

U.S. PATENT DOCUMENTS

| | | |
|---|---|---|
| 8,871,798 B2 | 10/2014 | Schoenafinger et al. |
| 2002/0026050 A1 | 2/2002 | Chackalamannil et al. |
| 2003/0216437 A1 | 11/2003 | Chackalamannil et al. |
| 2004/0006105 A1 | 1/2004 | Chackalamannil et al. |
| 2004/0152736 A1 | 8/2004 | Chackalamannil et al. |
| 2005/0267155 A1 | 12/2005 | Chelliah et al. |
| 2006/0079684 A1 | 4/2006 | Chackalamannil et al. |
| 2006/0106050 A1 | 5/2006 | Chakalamannil et al. |
| 2006/0106060 A1 | 5/2006 | Lansbury et al. |
| 2007/0149518 A1 | 6/2007 | Chackalamannil et al. |
| 2008/0090830 A1 | 4/2008 | Chackalamannil et al. |
| 2011/0301112 A1 | 12/2011 | Xia et al. |
| 2012/0157403 A1 | 6/2012 | Chackalamannil et al. |
| 2012/0184504 A1 | 7/2012 | Strony et al. |

FOREIGN PATENT DOCUMENTS

| | | |
|---|---|---|
| WO | WO2013134012 A1 | 9/2013 |
| WO | WO2015026686 A1 | 2/2015 |
| WO | WO2015026685 A8 | 5/2015 |

OTHER PUBLICATIONS

European Search Report for Application No. 14837743.5, Mailed Feb. 13, 2016, 7 pages.

PREPARATION AND USE OF 7A-AMIDE SUBSTITUTED- 6,6-DIFLUORO BICYCLIC HIMBACINE DERIVATIVES AS PAR-1 RECEPTOR ANTAGONISTS

CROSS REFERENCE TO RELATED APPLICATIONS

This application is a U.S. National Phase application under 35 U.S.C. §371 of PCT Application No. PCT/US14/051416 filed Aug. 18, 2014, which claims priority from U.S. Provisional Application Ser. No. 61/868,609, filed Aug. 22, 2013.

FIELD OF THE INVENTION

The present invention relates to 7a-amide substituted 6,6-difluro bicyclic himbacine derivatives, which are useful as protease activated receptor-1 (PAR-1) antagonists and might be expected to be cannabinoid ($CB_2$) receptor inhibitors. PAR-1 receptors are also known in the art as thrombin receptor antagonists (TRA). The inventive compounds have utility in treating disease states such as acute coronary syndrome (ACS) (unstable angina, non-ST-segment elevation [NSTE] myocardial infarction [MI], and ST segment-elevation myocardial infarction [STEMI]), secondary prevention of myocardial infarction or thrombotic stroke (secondary prevention) or peripheral artery disease (PAD), which is also know in the art as peripheral vascular disease. The present invention also relates to pharmaceutical compositions comprising the inventive compounds as well as processes for their preparation.

BACKGROUND OF THE INVENTION

Thrombin is known to have a variety of activities in different cell types. PAR-1 receptors are known to be present in such cell types as human platelets, vascular smooth muscle cells, endothelial cells and fibroblasts. The art indicates that PAR-1 receptor antagonists would be expected to be useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al., J. Med. Chem., 39 (1996), p. 4879-4887, tetra- and pentapeptides are disclosed as being potent thrombin receptor antagonists, for example N-trans-cinnamoyl-p-fluoroPhe-p-guanidinoPhe-Leu-Arg-$NH_2$ and N-trans-cinnamoyl-p-fluoroPhe-p-guanidinoPhe-Leu-Arg-Arg-$NH_2$. Peptide thrombin receptor antagonists are also disclosed in WO 94/03479.

Cannabinoid receptors belong to the superfamily of G-protein coupled receptors. They are classified into the predominantly neuronal $CB_1$ receptors and the predominantly peripheral $CB_2$ receptors. These receptors exert their biological actions by modulating adenylate cyclase and $Ca^{+2}$ and $K^+$ currents. While the effects of $CB_1$ receptors are principally associated with the central nervous system, $CB_2$ receptors are believed to have peripheral effects related to bronchial constriction, immunomodulation and inflammation. As such, the art suggests that a selective $CB_2$ receptor binding agent might be expected to have therapeutic utility in the control of diseases associated with rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis (R. G. Pertwee, Curr. Med. Chem. 6(8), (1999), 635; M. Bensaid, Molecular Pharmacology, 63 (4), (2003), 908).

Himbacine, a piperidine alkaloid of the formula

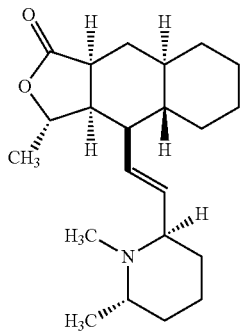 [SMILES: C[C@@H]1OC(=O)[C@H]2C[C@H]3CCCC[C@@H]3[C@@H](/C=C/[C@H]3CCC[C@H](C)N3C)[C@@H]12]

has been identified as a muscarinic receptor antagonist. The total synthesis of (+)-himbacine is disclosed in Chackalamannil et al., J. Am. Chem. Soc., 118 (1996), p. 9812-9813.

Substituted bi- and tricyclic thrombin receptors antagonists are known in the art to treat thrombin receptor mediated disorders such as thrombosis, atherosclerosis, restenosis, hypertension, angina pectoris, angiogenesis related disorders, arrhythmia, a cardiovascular or circulatory disease or condition, heart failure, ACS, myocardial infarction, glomerulonephritis, thrombotic stroke, thromboembolytic stroke, PAD, deep vein thrombosis, venous thromboembolism, a cardiovascular disease associated with hormone replacement therapy, disseminated intravascular coagulation syndrome and cerebral infarction, as well as $CB_2$ receptor mediated disorders. U.S. Pat. No. 6,645,987 and U.S. Pat. No. 6,894,065 disclose PAR-1 receptor antagonists of the structure:

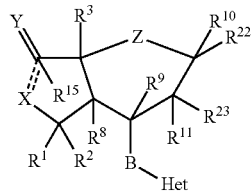

where $R^{10}$ may be groups such as H, alkyl, haloalkyl, hydroxyl, etc. and $R^{22}$ may be groups such as H, optionally substituted alkyl, hydroxyl, etc. Other known substituted thrombin receptor antagonists are disclosed in WO2001/96330, U.S. Pat. No. 6,063,847, U.S. Pat. No. 6,326,380, U.S. Pat. No. 7,037,920, U.S. Pat. No. 7,488,742, U.S. Pat. No. 7,713,999, U.S. Pat. No. 7,442,712, U.S. Pat. No. 7,488,752, U.S. Pat. Nos. 7,776,889, 7,888,369, U.S. Pat. No. 8,003,803 and U.S. Pat. No. 8,022,088. US 2008/0090830 and Chackalamannil et al., J. Med. Chem., 49 (2006), p. 5389. A PAR-1 receptor antagonist that exhibits good thrombin receptor antagonist activity (potency) and selectivity is vorapaxar (Merck & Co., Inc.), which has the following structure:

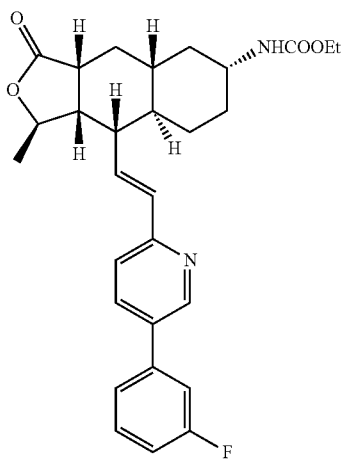

This compound underwent clinical trials and is disclosed in U.S. Pat. No. 7,304,048. A crystalline form of the bisulfate salt of vorapaxar is disclosed in U.S. Pat. No. 7,235,567.

WO2011/162,562 to LG Life Sciences LTD. describes a series of [6+5] fused bicycle derivatives of the general structure:

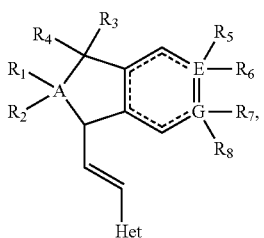

where $R_5$ and $R_6$ are inter alia both fluoro groups, as inhibitors of the PAR-1 receptor. The compounds are taught to be useful in the treatment and prevention of thrombus, platelet aggregation, atherosclerosis, restenosis, blood coagulation, hypertension, arrhythmia, angina pectoris, heart failure, inflammation and cancer when used alone or with other cardiovascular agents.

WO2011/28420 and WO2011/28421, both to Sanofi-Aventis, disclose compounds that are reported to be PAR-1 receptor antagonists. The compounds disclosed in WO2011/28420 are pyridyl-vinyl pyrazoloquinolines derivatives and have the following general structure:

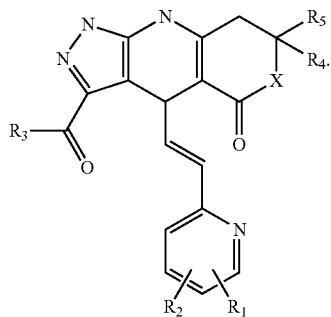

WO2011/28421 discloses tryicyclic pyridyl-vinyl-pyrrole derivatives of the following general structure:

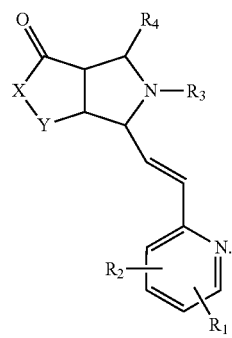

PCT/US13/027383 to Merck, Sharp & Dohme, Inc. discloses bicyclic himbacine derivatives of the following general structure

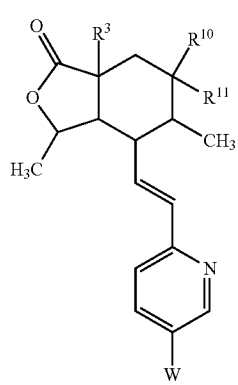

where $R^{10}$ and $R^{11}$ may both be fluoro groups. These compounds are PAR-1 receptor antagonists.

Applicants discovered in accordance with the present invention that the inventive compounds act as inhibitors of PAR-1 receptor and, based upon their structure, might also act as inhibitors of the $CB_2$ receptor. Therefore, the inventive compounds might be expected to be useful in treating disease states associated with the inhibition of these receptors.

There is a need for new compounds, formulations, treatment and therapies to treat diseases associated with the PAR-1 and $CB_2$ receptors. Moreover, there is a need to develop therapeutics that exhibit improved therapeutic profiles, such as desirable half-life and reduced unintended effects, such as drug-induced (acquired) long QT syndrome, which potentially can be fatal. It is, therefore, an object of this invention to provide compounds useful in the treatment, prevention or amelioration of such diseases or disorders with improved therapeutic profiles. These and other objectives will become evident from the following description.

SUMMARY OF THE INVENTION

In its many embodiments, the present invention provides for a novel group of bicyclic himbacine derivatives, which are PAR-1 receptor antagonists, or metabolites, stereoisomers, salts, solvates or polymorphs thereof, processes of preparing such compounds, pharmaceutical compositions comprising one or more such compounds, processes of preparing pharmaceutical compositions comprising one or more such compounds and potential methods of treatment, inhibition or amelioration of one or more disease states associated with the PAR-1 receptor by administering an effective amount at least one of the inventive bicyclic himbacine derivatives to a patient in need thereof.

In one aspect, the present application discloses a compound or a pharmaceutically acceptable salt, metabolite, solvate, prodrug or polymorph of said compound, said compound or pharmaceutically acceptable salt thereof having the general structure shown in Formula I

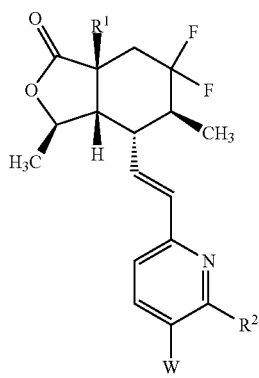

I wherein:
R$^1$ is —[C(R$^a$)(R$^b$)]$_x$—[C(R$^b$)(R$^b$)]$_y$—C(O)NH$_2$, or —N(H)—[(CH$_2$)]$_z$—C(O)—NH$_2$,
where:
R$^a$ is independently H, —C$_1$-C$_3$-alkyl, —OH or —C$_1$-C$_3$-alkoxy,
R$^b$ is independently H or —C$_1$-C$_3$-alkyl;
R$^2$ is H or alkyl (e.g., methyl);
W is

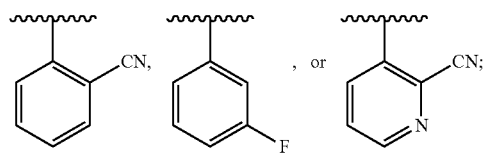

x is 0 or 1;
y is 0, 1, 2 or 3; and
z is 1 or 2
provided that when R$^a$ is OH or —C$_1$-C$_3$-alkoxy, x is 1.

Another aspect of the present invention is pharmaceutical compositions comprising a therapeutically effective amount of at least one compound of Formula I or a pharmaceutically acceptable salt thereof and a pharmaceutically acceptable carrier.

Another aspect of the present invention is pharmaceutical compositions comprising a therapeutically effective amount of at least one compound of Formula I or a pharmaceutically acceptable salt thereof, at least one additional cardiovascular agent and a pharmaceutically acceptable carrier.

Another aspect of the present invention is the possible prevention of one or more disease state associated with inhibiting the PAR-1 receptor by administering an effective amount of a compound of Formula I or a pharmaceutically acceptable salt thereof to a patient in need thereof.

Another aspect of the present invention is a method of inhibiting platelet aggregation comprising administering to a mammal an effective amount of a compound of Formula I or a pharmaceutically acceptable salt thereof.

It is further contemplated that the combination of the invention could be provided as a kit comprising in a single package at least one compound of Formula I or a pharmaceutically acceptable salt thereof in a pharmaceutical composition, and at least one separate pharmaceutical composition, such as, for example a separate pharmaceutical composition comprising a cardiovascular agent.

The compounds of the present invention can potentially be useful in the treatment, amelioration or prevention of one or more conditions associated with inhibiting the PAR-1 receptor by administering at least one compound of Formula I or a pharmaceutically acceptable salt thereof to a mammal in need of such treatment. Conditions that could potentially be treated or prevented by inhibiting the PAR-1 receptor include thrombosis, atherosclerosis, restenosis, hypertension, angina pectoris, angiogenesis related disorders, arrhythmia, a cardiovascular or circulatory disease or condition, heart failure, ACS, myocardial infarction, glomerulonephritis, thrombotic stroke, thromboembolytic stroke, PAD, deep vein thrombosis, venous thromboembolism, a cardiovascular disease associated with hormone replacement therapy, disseminated intravascular coagulation syndrome and cerebral infarction.

Another embodiment is the possible treatment, amelioration or prevention of ACS, secondary prevention of myocardial infarction or stroke, urgent coronary revascularization, or PAD by administering at least one compound of Formula I or a pharmaceutically acceptable salt thereof to a mammal in need of such treatment.

Another embodiment of this invention is in the possible treatment, amelioration or prevention of one or more conditions associated with cardiopulmonary bypass surgery (CPB) by administering effective amount of at least one compound of Formula I or a pharmaceutically acceptable salt thereof to a subject of said CPB surgery. CPB surgery includes coronary artery bypass surgery (CABG), cardiac valve repair and replacement surgery, pericardial and aortic repair surgeries. The conditions associated with CABG include bleeding, thrombotic vascular events (such as thrombosis or restenosis), vein graft failure, artery graft failure, atherosclerosis, angina pectoris, myocardial ischemia, acute coronary syndrome, myocardial infarction, heart failure, arrhythmia, hypertension, transient ischemic attack, cerebral function impairment, thromboembolic stroke, cerebral ischemia, cerebral infarction, thrombophlebitis, deep vein thrombosis and PAD.

Another embodiment of the present invention is the possible use of a compound of Formula I or a pharmaceutically acceptable salt thereof for the manufacture of a medicament for the treatment, amelioration or prevention of one or more conditions associated with inhibiting the PAR-1 receptor in a patient.

DETAILED DESCRIPTION

In an embodiment, the present invention provides compounds represented by structural Formula I, or pharmaceutically acceptable salt thereof, wherein the various moieties are as described as above.

Another embodiment of the present invention is the following compounds or a pharmaceutically acceptable salt thereof:
(1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-carboxamide (1);

(1R,3aR,6S,7R,7aS)-7-((E)-2-(5-(2-cyanophenyl)-6-methylpyridin-2-yl)vinyl)-5,5-difluoro-1,6-dimethyl-3-oxooctahydroisobenzofuran-3a-carboxamide (4);

2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)acetamide (5)

2-((1R,3aR,6S,7R,7aS)-5,5-difluoro-7-((E)-2-(5-(3-fluorophenyl)pyridin-2-yl)vinyl)-1,6-dimethyl-3-oxooctahydroisobenzofuran-3a-yl)acetamide (6)

2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)propanamide (7);

R or S)-2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)propanamide (8);

(S or R)-2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)propanamide (9);

1R,3aR,6S,7R,7aS)-7-((E)-2-(2'-cyano-[3,3'-bipyridin]-6-yl)vinyl)-5,5-difluoro-1,6-dimethyl-3-oxooctahydroisobenzofuran-3a-carboxamide (11);

3-((1R,3aR,6S,7R,7aS)-7-((E)-2-(2'-cyano-[3,3'-bipyridin]-6-yl)vinyl)-5,5-difluoro-1,6-dimethyl-3-oxooctahydroisobenzofuran-3a-yl)propanamide (15);

2-((1R,3aR,6S,7R,7aS)-7-((E)-2-(2'-cyano-[3,3'-bipyridin]-6-yl)vinyl)-5,5-difluoro-1,6-dimethyl-3-oxooctahydroisobenzofuran-3a-yl)acetamide (17);

2-(((1R,3aS,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)amino)acetamide (18);

(S and R)-2-((1R,3aR,6S,7R,7aS)-7-((E)-2-(5-(2-cyanophenyl)pyridin-2-yl)vinyl)-5,5-difluoro-1, 6-dimethyl-3-oxooctahydroisobenzofuran-3a-yl)-2-methoxyacetamide (19);

(R and S)-2-((1R,3aR,6S,7R,7aS)-7-((E)-2-(5-(2-cyanophenyl)pyridin-2-yl)vinyl)-5,5-difluoro-1, 6-dimethyl-3-oxooctahydroisobenzofuran-3a-yl)-2-hydroxyacetamide (20); or 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methylpropanamide (21).

Another embodiment is a compound of Formula I or a pharmaceutically acceptable salt thereof wherein $R^1$ is —$(CH_2)_a$—C(O)—$NH_2$ and a is 0, 1 or 2.

Another embodiment is a compound of Formula I or a pharmaceutically acceptable salt thereof wherein $R^1$ is —(NH)—$[CH_2]_z$—C(O)—$NH_2$ and z is 1 or 2.

Another embodiment is a compound of Formula I or a pharmaceutically acceptable salt thereof wherein $R^1$ is —CH($CH_3$)—C(O)—$NH_2$ or —C($CH_3$)($CH_3$)—C(O)—$NH_2$.

Another embodiment is a compound of Formula I or a pharmaceutically acceptable salt thereof wherein $R^1$ is —CH(OH)—C(O)—$NH_2$ or —CH($OCH_3$)—C(O)—$NH_2$.

Another embodiment is a compound of or a pharmaceutically acceptable salt thereof wherein W is

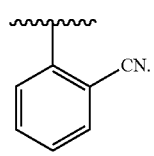 [SMILES: *c1ccccc1C#N]

Another embodiment is a compound of Formula I or a pharmaceutically acceptable salt thereof wherein W is

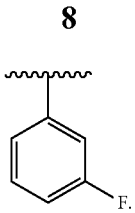

Another embodiment is a compound of Formula I or a pharmaceutically acceptable salt thereof wherein W is

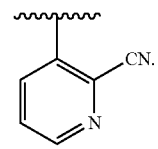 [SMILES: *c1cccnc1C#N]

As used above, and throughout this disclosure, the following terms, unless otherwise indicated, shall be understood to have the following meanings:

"Subject" includes both humans and animals.

"Mammal" means humans and other mammalian animals.

"Alkyl" is intended to include both branched- and straight-chain saturated aliphatic hydrocarbon groups having, e.g., 1-12. 1-6, or 1-3 carbon atoms. "Branched" means that one or more lower alkyl groups such as methyl, ethyl or propyl, are attached to a linear alkyl chain. "Lower alkyl" means a group having about 1 to about 6 carbon atoms in the chain which may be straight or branched.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Halo" refers to —F, —Cl, —Br or —I. Non-limiting examples include —F or —Cl.

"Halogen" means fluorine, chlorine, bromine, or iodine. Non-limiting examples include fluorine or chlorine.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterized by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

"Effective amount" or "therapeutically effective amount" is meant to describe an amount of compound or a composition of the present invention effective as PAR-1 or thrombin receptor antagonists, thereby producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

In this application, unless otherwise indicated, whenever there is a structural formula provided, such as those of Formula I, this formula is intended to encompass all forms of a compound such as, for example, any solvates, hydrates, stereoisomers, tautomers, co-crystals, polymorphs etc.

Compounds of Formula I, and salts, solvates, co-crystals and prodrugs thereof, may exist in their tautomeric form (for example, as an amide or imino ether). All such tautomeric forms are contemplated herein as part of the present invention.

Prodrugs, solvates and co-crystals of the compounds of the invention are also contemplated herein. The term "prodrug", as employed herein, denotes a compound that is a drug precursor which, upon administration to a subject, undergoes chemical conversion by metabolic or chemical processes to yield a compound of Formula I or a salt thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

A co-crystal is a crystalline superstructure formed by combining an active pharmaceutical intermediate with an inert molecule and provides crystallinity to the combined form. Co-crystals are often made between a dicarboxlyic acid such as fumaric acid, succinic acid etc. and a basic amine such as the one represented by compounds of this invention in different proportions depending on the nature of the co-crystal. (Remenar, J. F. et. al. *J Am. Chem. Soc.* 2003, 125, 8456).

All stereoisomers (for example, geometric isomers, optical isomers and the like) of the present compounds (including those of the salts, solvates, co-crystals and prodrugs of the compounds as well as the salts and solvates, co-crystals of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}$C or $^{18}$F can be useful for application in Positron Emission Tomography (PET) and those labeled with gamma ray emitting isotopes like $^{123}$I can be useful for application in Single photon emission computed tomography (SPECT). Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically-labeled compounds of Formula (I), in particular those containing isotopes with longer half lives (T1/2>1 day), can generally be prepared by following procedures analogous to those disclosed in the Schemes and/or in the Examples herein below, by substituting an appropriate isotopically labeled reagent for a non-isotopically labeled reagent.

As discussed above, the compounds of Formula I may be used to treat, ameliorate or prevent conditions associated with inhibiting the PAR-1 receptor. In addition to the conditions mentioned above, other conditions could include migraine, erectile dysfunction, rheumatoid arthritis, rheumatism, astrogliosis, a fibrotic disorder of the liver, kidney, lung or intestinal tract, systemic lupus erythematosus, multiple sclerosis, osteoporosis, renal disease, acute renal failure, chronic renal failure, renal vascular homeostasis, renal ischemia, bladder inflammation, diabetes, diabetic neuropathy, cerebral stroke, cerebral ischemia, nephritis, cancer, melanoma, renal cell carcinoma, neuropathy, malignant tumors, neurodegenerative and/or neurotoxic diseases, conditions or injuries, Alzheimer's disease, an inflammatory disease or condition, asthma, glaucoma, macular degeneration, psoriasis, endothelial dysfunction disorders of the liver, kidney or lung, inflammatory disorders of the lungs and gastrointestinal tract, respiratory tract disease or condition, radiation fibrosis, endothelial dysfunction, periodontal diseases or wounds, or a spinal cord injury, or a symptom or result thereof, viral infections, including infections from human respiratory syncytial virus (hRSV), human metapneumovirus (hMPV) and influenza virus type A, as well as other disorders in which thrombin and its receptor play a pathological role.

In addition to their PAR-1 receptor antagonist properties, the compounds of Formula I or the pharmaceutically acceptable salts might be expected to be used to treat, ameliorate or prevent one or more conditions associated with inhibiting the $CB_2$ receptor by administering at least one compound of Formula I or a pharmaceutically acceptable salt thereof to a mammal in need of such treatment. Conditions might include, for example, rheumatoid arthritis, systemic lupus erythematosus, multiple sclerosis, diabetes, osteoporosis, renal ischemia, cerebral stroke, cerebral ischemia, nephritis, inflammatory disorders of the lungs and gastrointestinal tract, and respiratory tract disorders such as reversible airway obstruction, chronic asthma and bronchitis.

In another embodiment, compounds of the present invention might be expected to be useful in a method for treating, ameliorating or preventing radiation- and/or chemical-induced toxicity in non-malignant tissue in a patient comprising administering a therapeutically effective amount of at least one compound of Formula I or a pharmaceutically acceptable salt thereof. In particular, the radiation- and/or chemical-induced toxicity is one or more of intestinal fibrosis, pneumonitis, and mucositis. In one embodiment, the radiation- and/or chemical-induced toxicity is intestinal fibrosis. In another embodiment, the radiation- and/or chemical-induced toxicity is oral mucositis. In yet another embodiment, the radiation- and/or chemical-induced toxicity is intestinal mucositis, intestinal fibrosis, intestinal radiation syndrome, or pathophysiological manifestations of intestinal radiation exposure.

The present invention might also be expected to provide for methods for reducing structural radiation injury in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for reducing inflammation in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for adverse tissue remodeling in a patient that will be exposed, is concurrently exposed, or was exposed to radiation and/or chemical toxicity, comprising administering a therapeutically effective amount of at least one compound of Formula I or a pharmaceutically acceptable salt thereof. The present invention might also be expected to provide for methods for reducing fibroproliferative tissue effects in a patient that will be exposed, is concurrently exposed, or was exposed to radiation and/or chemical toxicity, comprising administering a therapeutically effective amount of at least one compound of Formula I or a pharmaceutically acceptable salt thereof.

The present invention might also be expected to provide for methods useful for treating a cell proliferative disorder in a patient suffering therefrom comprising administering a therapeutically effective amount of at least one compound of Formula I or a pharmaceutically acceptable salt thereof. In one embodiment, the cell proliferative disorder is pancreatic cancer, glioma, ovarian cancer, colorectal and/or colon cancer, breast cancer, prostate cancer, thyroid cancer, lung cancer, melanoma, or stomach cancer. In one embodiment, the glioma is an anaplastic astrocytoma. In another embodiment, the glioma is a glioblastoma multiforme.

As used above, the term inflammatory disease or condition includes irritable bowel syndrome, Crohn's disease, nephritis or a radiation- or chemotherapy-induced proliferative or inflammatory disorder of the gastrointestinal tract, lung, urinary bladder, gastrointestinal tract or other organ. The term respiratory tract disease or condition includes reversible airway obstruction, asthma, chronic asthma, bronchitis or chronic airways disease. "Cancer" includes renal cell carcinoma or an angiogenesis related disorder. "Neurodegenerative disease" includes Parkinson's disease, amyotropic lateral sclerosis, Alzheimer's disease, Huntington's disease or Wilson's disease.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically acceptable carrier. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The amount and frequency of administration of the compound of this invention and/or their pharmaceutically acceptable salts will be regulated according to the judgment of the attending clinician considering such factors as age, condition and size of the patient as well as the severity of the symptoms being treated.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The term "patient" includes animals, preferably mammals and especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk of said disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing" or "prevention" are used herein to refer to administering a compound before the onset of clinical symptoms.

The compounds of this invention may also be useful in combination (administered together or sequentially) with one or more therapeutic agents, such as, for example, another cardiovascular agent. Cardiovascular agents that could be used in combination with the compounds for Formula I or their pharmaceutically acceptable salts include drugs that have anti-thrombotic, anti-platelet aggregation, anti-atherosclerotic, anti-restenotic and/or anti-coagulant activity. Such drugs are useful in treating thrombosis-related diseases including thrombosis, atherosclerosis, restenosis, hypertension, angina pectoris, arrhythmia, heart failure, myocardial infarction, glomerulonephritis, thrombotic and thromboembolic stroke, peripheral vascular diseases, other cardiovascular diseases, cerebral ischemia, inflammatory disorders and cancer, as well as other disorders in which thrombin and its receptor play a pathological role. Suitable cardiovascular agents are selected from the group consisting of thromboxane A2 biosynthesis inhibitors such as aspirin; thromboxane antagonists such as seratrodast, picotamide and ramatroban; adenosine diphosphate (ADP) inhibitors such as clopidogrel; cyclooxygenase inhibitors such as aspirin, meloxicam, rofecoxib and celecoxib; angiotensin antagonists such as valsartan, telmisartan, candesartan, irbesartran, losartan and eprosartan; endothelin antagonists such as tezosentan; phosphodiesterase inhibitors such as milrinoone and enoximone; angiotensin converting enzyme (ACE) inhibitors such as captopril, enalapril, enaliprilat, spirapril, quinapril, perindopril, ramipril, fosinopril, trandolapril, lisinopril, moexipril and benazapril; neutral endopeptidase inhibitors such as candoxatril and ecadotril; anti-coagulants such as ximelagatran, fondaparin and enoxaparin; diuretics such as chlorothiazide, hydrochlorothiazide, ethacrynic acid, furosemide and amiloride; platelet aggregation inhibitors such as abciximab and eptifibatide; and GP IIb/IIIa antagonists.

Other possible combinations might include lipid lowering agents (e.g., simvastatin, lovastatin, pravastatin, atorvastatin rosuvastatin, pitavastatin, ezetimibe); niacin in immediate-release or controlled release forms or niacin in combination with a DP antagonist, such as laropiprant and/or with an HMG-CoA reductase inhibitor; niacin receptor agonists such as acipimox and acifran, as well as niacin receptor partial agonists; metabolic altering agents including insulin sensitizing agents and related compounds (e.g., muraglitazar, glipizide, stigliptin, metformin, rosiglitazone statins, e.g., simvastatin, atorvastatin and rosovastatin), PCSK9 inhibitors, e.g. antibodies—REGN727, AMG-145, RN316, RG7652; and small molecule inhibitors and CETP inhibitors, e.g., anacetrapib, evacetrapib, etc. Other possible combinations include AMPK agonists (e.g., ETC-1002); glucagon receptor antagonists; Lp-PLA2 inhibitors (e.g., darapladib) and anti-IL-1beta antibodies (canakinumab).

The dosage of the cardiovascular agent can be determined from published material, and may range from 1 to 1000 mg per dose.

An embodiment is combinations comprising an effective amount of a compound of Formula I or a pharmaceutically acceptable salt thereof and an ADP antagonist and/or cyclooxygenase inhibitor.

Non-limiting combinations comprises an effective amount of a compound according to Formula I or a pharmaceutically acceptable salt thereof and aspirin, ticagrelor, cangrelor, clopidogrel (either as a free base or as a pharmaceutically acceptable salt, such as its bisulfate salt), prasugrel, ticlopidine or fragmin.

Other therapeutic agents could include drugs that are known and used in the treatment of inflammation, rheumatism, asthma, glomerulonephritis, osteoporosis, neuropathy and/or malignant tumors, angiogenesis related disorders, cancer, disorders of the liver, kidney and lung, melanoma, renal cell carcinoma, renal disease, acute renal failure, chronic renal failure, renal vascular homeostasis, glomerulonephritis, chronic airways disease, bladder inflammation, neurodegenerative and/or neurotoxic diseases, conditions, or injuries, radiation fibrosis, endothelial dysfunction, periodontal diseases and wounds. Further examples of therapeutically effective agents which may be administered in combination with a compound of Formula I or a pharmaceutically acceptable salt thereof include resistance factors for tumor cells towards chemotherapy and proliferation inhibitors of smooth muscle cells, endothelial cells, fibroblasts, kidney cells, osteosarcoma cells, muscle cells, cancer cells and/or glial cells.

For treating and/or preventing radiation- and/or chemical-induced toxicity in non-malignant tissue, the present invention includes administering to a patient in need of such treatment an effective amount of a combination of one or more compounds of formula I and one or more radiation-response modifiers selected from the group consisting of Kepivance™ (palifermin), L-glutamine, teduglutide, sucralfate mouth rinses, iseganan, lactoferrin, mesna and trefoil factor.

For treating a cell proliferative disorder the present invention includes administering to a patient in need of such treatment an effective amount of a combination of one or more compounds of Formula I or a pharmaceutically acceptable salt thereof and another antineoplastic agent. In one embodiment, the other antineoplastic agent is temozolomide and the cell proliferative disorder is glioma. In another embodiment, the other antineoplastic agent is interferon and the cell proliferative disorder is melanoma. In one embodiment, the other antineoplastic agent is PEG-Intron (peginterferon alpha-2b) and the cell proliferative disorder is melanoma.

Pharmaceutical compositions comprising a therapeutically effective amount of a combination of at least one compound of Formula I or a pharmaceutically acceptable salt thereof and a radiation-response modifier in a pharmaceutically acceptable carrier are also provided.

Pharmaceutical compositions comprising a therapeutically effective amount of a combination of at least one compound of Formula I or a pharmaceutically acceptable salt thereof and an antineoplastic agent in a pharmaceutically acceptable carrier are also provided.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

In general, the compounds in the invention may be produced by a variety of processes know to those skilled in the art and by know processes analogous thereto. The invention disclosed herein is exemplified by the following preparations and examples which should not be construed to limit the scope of the disclosure. Alternative mechanistic pathways and analogous structures will be apparent to those skilled in the art.

The practitioner is not limited to these methods.

Moreover, one skilled in the art would have resources such as *Chemical Abstracts* or *Beilstein* at his or her disposal to assist in preparing a specific compound.

One skilled in the art will recognize that one route will be optimized depending on the choice of appendage substituents. Additionally, one skilled in the art will recognize that in some cases the order of steps has to be controlled to avoid functional group incompatibility.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme and in the preparations and examples described below.

Where NMR data are presented, 1H spectra were obtained, for example, on either a Varian Inova (400 or 500 mHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed, for example, using an Agilent 1100 series or Applied Biosystems® API-100 mass spectrometer and C18 column, 5-95% $CH_3CN$—$H_2O$ (with 0.05% TFA) gradient. The observed parent ion is given Throughout the synthetic schemes, abbreviations are used with the following meaning unless otherwise indicated: ACN or MeCN=acetonitrile; Aq.=aqueous; t-Butyl=tert-butyl; t-BuOH=tert-butyl alcohol; cat.=catalyst; DBU=1,8-Diazabicyclo[5.4.0]undec-7-ene; DCC=N,N'-bicyclohexylcarbodiimide; DCM=dichloromethane; DAST=diethylaminosulfur trifluoride; DMAC=N,N-dimethylacetamide; DMAP=4-dimethylamino pyridine; DMF=dimethylformamide; DMP=Dess-Martin periodinane; DMSO=dimethylsulfoxide; DIEA=N,N-Diisopropylethylamine or Hünig's base; Et=ethyl; EtOH=ethanol; EtOAc=ethyl acetate; g=gas HATU=O-(7-azabenzotriazol-1-yl)-N,N,N',N'-tetramethyluronium hexafluorophosphate; HEPES=(4-(2-hydroxyethyl)-1-piperazineethanesulfonic acid); HPLC=high pressure liquid chromatography; HOAc=acetic acid; LCMS=liquid chromatorgraphy-mass spectrometry; KHMDS=Potassium bis(trimethylsilyl)amide; LiHMDS=lithium bis(trimethylsilyl)amide; Me=methyl; MeOH=methanol; MeI=methyl iodide; mmol=millimoles MPLC=medium pressure liquid chromatography; Ms=mesylate; MS ESI=electrospray ionixation mass spectrometry; MTBE=methyl tert-butyl ether; NMP=N-methyl-2-pyrrolidone; Ph=phenyl; piv-cl=pivaloyl chloride; i-Pr=iso-propyl; RT or rt=room temperature TEA=triethanolamine; TFA=trifluoroacetic acid; THF=tetrahydrofuran; TLC=thin layer chromatography; and X=times.

Intermediate Syntheses

Intermediate compounds of the present invention can be synthesized according to the schemes and procedures outlined below. Since the schemes are an illustration, the invention should not be construed as being limited by the chemical reactions and conditions expressed. The preparation of the various starting materials used in the schemes is well within the ordinary skill level of a practitioner of this art. Unless otherwise indicated, the definition for a variable is the same as that provided in Formula I.

SCHEME A

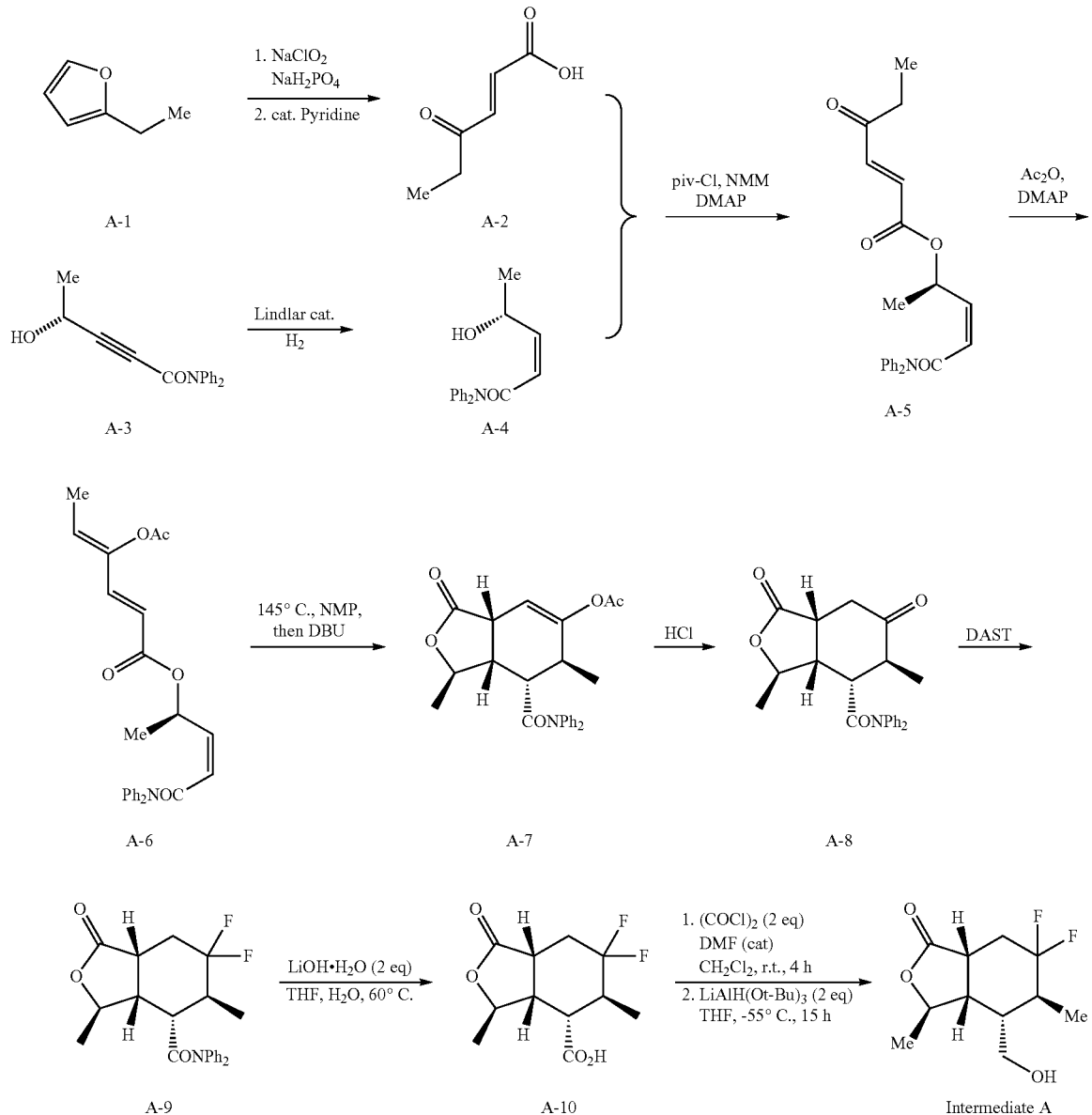

Intermediate A can be prepared from commercially available and known starting materials according to Scheme A. 2-Ethylfuran (A-1) was oxidized to the corresponding hydroxyfuranone, which under the action of base is opened to carboxylic acid (A-2). Alkynylalcohol (A-3) was reduced to the corresponding cis-alkene (A-4) using Lindlar's catalyst under an atmosphere of hydrogen gas. DCC-mediated coupling of prepared intermediates (A-2) and (A-4) provided the complete carbon framework for intermediate A in compound (A-5). Formation of the enol acetate (A-6) set the stage for an intramolecular Diels-Alder reaction to form lactone (A-7). Hydrolysis and subsequent reaction of ketone (A-8) with DAST provided the C6-difluoro lactone (A-9). Saponification of the amide provided carboxylic acid (A-10), which was then chemoselectively reduced via a two-step protocol to yield Intermediate A.

Step 1: 5-ethyl-5-hydroxyfuran-2(5H)-one

NaH$_2$PO$_4$ (243 g, 3.12 mol) was added to a solution of 2-ethylfuran (100 g, 1.04 mol) in t-BuOH (1.0 L) and H$_2$O (200 mL) at room temperature. After 30 min, NaClO$_2$ (312 g, 3.12 mol) was added portionwise. The temperature was controlled between 10-30° C. After the addition, the reaction was stirred for another 2 h until the reaction goes to completion. The reaction solution was purged with $N_2$ overnight until it turned to white. The precipitate was filtered and t-BuOH was removed under vacuo. The reaction was extracted with $CH_2Cl_2$ and dried with anhydrous $Na_2SO_4$. After combining all thirteen reactions and concentration, the title compound was obtained and was used directly for the next step without further purification.

Step 2: (E)-4-oxohex-2-enoic acid

To a solution of 5-ethyl-5-hydroxyfuran-2(5H)-one (130 g, 1.02 mol) in THF (645 mL) was added acetone (520 mL), water (130 mL), pyridine (8.1 mL, 0.1 mol) at room temperature. The reaction was stirred overnight. TLC (petroleum ether/ethyl acetate, 3:1) showed the reaction was completed. The mixture was concentrated under vacuo. The residue was treated with 10% $K_2CO_3$ to pH>10 at 0° C. and extracted with ethyl acetate (500 mL×3). The aqueous layer was acidified with concentrated HCl at 0° C. to pH<2. After extraction with ethyl acetate (500 mL×6) and washed with brine, the organic layer was dried with anhydrous $Na_2SO_4$ and concentrated to give the title compound. It was washed with methyl tert-butyl ether to provide the title compound. $^1$H NMR (400 MHz, $CDCl_3$) δ 7.12 (d, 1H, J=16.0 Hz), 6.66 (d, 1H, J=15.6 Hz), 2.68 (q, 2H, J=7.2 Hz), 1.13 (q, 2H, J=7.2 Hz).

Step 3: (R,Z)-4-hydroxy-N,N-diphenylpent-2-enamide

To a solution of (R)-4-hydroxy-N,N-diphenylpent-2-ynamide (200 g, 0.75 mol) and Lindlar catalyst (13.6 g, 7.5 mmol) in $CH_3OH$ (2 L) was added quinoline (21.6 mL, 182 mmol) at room temperature. The reaction was evacuated and recharged with a balloon of $H_2$. After stirring at room temperature for 1 h, TLC (petroleum ether/ethyl acetate, 3:1) showed the reaction was complete. Solvent was removed under reduced pressure at 35° C. THF (1 L) was added which was followed by the addition of petroleum ether (1 L). After removing half amount of the solvent, petroleum ether (1 L) was added. A precipitate formed during concentration, which was filtered and washed with methyl tert-butyl ether to afford the title compound. The combined filtrate residues were purified by silica gel column chromatography (petroleum ether:ethyl acetate, 5:1) to yield another batch of (R,Z)-4-hydroxy-N,N-diphenylpent-2-enamide. $^1$H NMR (400 MHz, $CDCl_3$) δ 7.38-7.23 (m, 10H), 6.09 (dd, 1H, J=12.0, 6.0 Hz), 5.82 (d, 1H, J=12.0 Hz), 4.88-4.85 (m, 1H), 1.35 (d, 1H, J=6.8 Hz).

Step 4: (E)-(R,Z)-5-(diphenylamino)-5-oxopent-3-en-2-yl 4-oxohex-2-enoate

NMM (91 mL, 814 mmol) was added to (E)-4-oxohex-2-enoic acid (58 g, 450 mmol) in anhydrous toluene (800 mL) at 0° C. Then, pivaloyl chloride (55 mL, 450 mmol) was added dropwise while maintaining the internal temperature between 0-5° C. After the addition, the reaction was stirred at 0° C. for 30 min. (R,Z)-4-Hydroxy-N,N-diphenylpent-2-enamide (100 g, 370 mmol) and DMAP (4.57 g, 37 mmol) in anhydrous toluene (400 mL) and anhydrous THF (200 mL) were added dropwise to the reaction mixture while maintaining the temperature between 0-5° C. under $N_2$. After 2 hours, the TLC (petroleum ether:ethyl acetate, 5:1) showed that the reaction was complete. 9 N $H_2SO_4$ (330 mL) was added dropwise to quench the reaction, while the temperature was kept between 0-5° C. The reactions were combined together and extracted with methyl tert-butyl ether and washed with saturated $NaHCO_3$. The crude product was purified by silica gel column chromatography (petroleum ether:ethyl acetate, 15:1) to give the title compound. $^1$H NMR (400 MHz, $CDCl_3$) δ 7.34-7.24 (m, 10H), 7.06 (dd, 1H, J=16.0, 4.0 Hz), 6.66 (dd, 1H, J=16.0, 4.0 Hz), 6.35-6.32 (m, 1H), 5.88-5.80 (m, 2H), 2.68-2.63 (m, 2H), 1.49-1.47 (m, 3H), 1.13-1.08 (m, 3H).

Step 5: (2E,4Z)—(R,Z)-5-(diphenylamino)-5-oxopent-3-en-2-yl 4-acetoxyhexa-2,4-dienoate (E)-(R,Z)-5-(Diphenylamino)-5-oxopent-3-en-2-yl 4-oxohex-2-enoate (100 g, 265 mmol) and DMAP (9.5 g, 79 mmol) in $Ac_2O$ (100 mL, 1.06 mol) were stirred at 50° C. for 19 h. TLC (petroleum ether:ethyl acetate, 5:1) showed the reaction was complete. The reaction was concentrated under reduced pressure at 45° C. The reaction was extracted with methyl tert-butyl ether and washed with 10% citric acid (5 L). The organic layer was washed with sat. $NaHCO_3$, brine, dried over $Na_2SO_4$ and filtered, the reaction was concentrated to give the title compound, which was used without further purification in the next step. $^1$H NMR (400 MHz, $CDCl_3$) δ 7.25-7.15 (m, 10H), 6.26-6.23 (m, 1H), 5.87-5.73 (m, 4H), 2.27 (s, 3H), 1.69 (d, 1H, J=6.8 Hz), 1.46 (d, 1H, J=6.4 Hz).

Step 6: (1R,3aS,6S,7R,7aS)-7-(diphenylcarbamoyl)-1,6-dimethyl-3-oxo-1,3,3a,6,7,7a-hexahydroisobenzofuran-5-yl acetate (2E,4Z)—(R,Z)-5-(Diphenylamino)-5-oxopent-3-en-2-yl 4-acetoxyhexa-2,4-dienoate (100 g, 0.24 mol) in NMP (2.5 L) was stirred at 145° C. for 2 h. The TLC (petroleum ether:ethyl acetate, 3:1) showed the reaction was almost complete. The reaction was cooled to 50° C. and DBU (3.6 mL, 2.39 mmol) was added in one portion. After 1 h, the reaction was cooled to 20° C. and was poured to cold water (22 L). The reaction was extracted with ethyl acetate (22 L). The organic layer was washed with water (22 L×2). The combined aqueous layers were extracted with ethyl acetate (5 L×3). The organic layers were combined, washed with brine and dried with anhydrous $Na_2SO_4$. After concentration, a precipitate that had formed was washed with methyl tert-butyl ether to give the title compound. The filtrate was concentrated and purified by silica gel column chromatography (petroleum ether:$CH_2Cl_2$, 6:1) to give another batch of the title compound. $^1$H NMR (400 MHz, $CDCl_3$) δ 7.51-7.23 (m, 10H), 5.26 (s, 1H), 4.90-4.86 (m, 1H), 3.21-3.10 (m, 2H), 2.83 (dd, 1H, J=10.8, 3.6 Hz), 2.52-2.50 (m, 1H), 2.16 (s, 3H), 1.58 (d, 3H, J=6.0 Hz), 1.09 (d, 3H, J=6.4 Hz).

Step 7: (3R,3aS,4R,5S,7aR)-3,5-dimethyl-1,6-dioxo-N,N-diphenyloctahydroisobenzofuran-4-carboxamide HCl (298 mL, 4 M in water) was added dropwise to (1R,3aS,6S,7R,7aS)-7-(diphenylcarbamoyl)-1, 6-dimethyl-3-oxo-1,3,3a,6,7,7a-hexahydroisobenzofuran-5-yl acetate (100 g, 238 mmol) in $CH_3OH$ (1 L) at 0° C. After the addition, the reaction was warmed to room temperature and stirred for another 36 h. The TLC (petroleum ether:ethyl acetate, 3:1) showed the reaction was almost complete. Methanol was removed under reduced pressure at 35° C.

The reaction was extracted with $CH_2Cl_2$ and the organics was washed with sat. $NaHCO_3$, brine, dried over $Na_2SO_4$ and concentrated. The resultant residue was purified on multiple 15 g scale silica gel columns (petroleum ether: $CH_2Cl_2$, 6:1) to yield the title compound. MS ESI calcd. for $C_{23}H_{24}NO_4$ $[M+H]^+$ 378. found 378. $^1$H NMR (400 MHz, $CDCl_3$) δ 7.50-7.46 (m, 3H), 7.35-7.33 (m, 2H), 7.29-7.22 (m, 5H), 5.16-5.10 (m, 1H), 2.98-2.90 (m, 3H), 2.65-2.63 (m, 1H), 2.55-2.46 (m, 2H), 1.56 (d, 3H, J=5.6 Hz), 1.18-1.14 (m, 3H).

Step 8: (3R,3aS,4R,5S,7aR)-6,6-difluoro-3,5-dimethyl-1-oxo-N,N-diphenyloctahydroisobenzofuran-4-carboxamide To a solution of (3R,3aS,4R,5S,7aR)-3,5-dimethyl-1,6-dioxo-N,N-diphenyloctahydroisobenzofuran-4-carboxamide (300.0 g, 0.79 mol) in $CH_2Cl_2$ (anhyd., 3 L) was added DAST (180 mL, 2.37 mol) dropwise slowly at 15-30° C. The resulting mixture was stirred overnight at 25° C. After LCMS showed the mixture was complete, the mixture was slowly poured to a solution of $K_3PO_4.3H_2O$ (0.4 mol/L, 3 L) and was partitioned with water and $CH_2Cl_2$. The aqueous layer was extracted with $CH_2Cl_2$ (1000 mL×2). The combined organic layers were washed with $NaHCO_3$ (500 mL), brine (500 mL), dried over $Na_2SO_4$, filtered and concentrated under reduced pressure. The residue was oxidized by $KMnO_4$ (100 g) in DMAC for 2 hours, then filtered. The filtrate was extracted by EtOAc, washed with 10% $CaCl_2$ aqueous solution, and brine. The combined organic solution was dried by $Na_2SO_4$ and concentrated. The residue was further purified by recrystallization with ethanol (3 V) to give the title compound. $^1$H NMR (400 MHz, $CDCl_3$) δ 7.40 (m, 3H), 7.24 (m, 7H), 4.84 (m, 1H), 2.76 (m, 1H), 2.45 (m, 3H), 2.18 (m, 1H), 1.71 (m, 1H), 1.5 (d, 3H, J=5.6 Hz), 1.1 (d, 3H, J=6.5 Hz).

Step 9: (3R,3aR,4R,5S,7aR)-6,6-difluoro-3,5-dimethyl-1-oxooctahydroisobenzofuran-4-carboxylic acid To a solution of the (3R,3aS,4R,5S,7aR)-6,6-difluoro-3,5-dimethyl-1-oxo-N,N-diphenyloctahydroisobenzofuran-4-carboxamide (260 g, 0.653 mol) in THF (1300 mL) was added a solution of $LiOH.H_2O$ (55 g, 1.31 mol) in $H_2O$ (650 mL) at room temperature. The mixture was heated to 60° C. and stirred for 2 h. Upon completion of reaction, the mixture was diluted with $LiOH.H_2O$ solution (1.3 L, 10% in water). The THF layer was removed in vacuo. The aqueous phase was extracted with MTBE (800 mL×3). The aqueous layer was acidified to pH 1-2 with 1N HCl and extracted with EtOAc (800 mL mL×3). The combined organic layers were washed with water (500 mL), brine (500 mL), dried over $Na_2SO_4$, filtered and concentrated to give the title compound. $^1$H NMR (400 MHz, $CDCl_3$) δ 4.73 (m, 1H), 2.99 (m, 1H), 2.89 (m, 1H), 2.64 (m, 1H), 2.53 (m, 1H), 2.33 (m, 1H), 1.86 (m, 1H), 1.39 (d, 3H), 1.15 (d, 3H).

Step 10: (3R,3aS,4R,5S,7aR)-6,6-difluoro-4-(hydroxymethyl)-3,5-dimethylhexahydroisobenzofuran-1(3H)-one To a solution of (3R,3aR,4R,5S,7aR)-6,6-difluoro-3,5-dimethyl-1-oxooctahydroisobenzofuran-4-carboxylic acid (81.0 g, 0.326 mol) in $CH_2Cl_2$ (800 mL) was added $(COCl)_2$ (58.8 mL, 0.66 mol) and DMF (1 mL) at 20-25° C. under nitrogen. The mixture was stirred for 4 hours. Upon reaction completion, the mixture was concentrated under reduced pressure. The residue was dissolved with THF (400 mL×2) and then concentrated twice. The residue was dissolved in THF (500 mL), and a solution of $LiAlH(t-BuO)_3$ (653 mL, 0.653 mol, 1 M in THF) was added dropwise slowly below −55° C. under nitrogen. The mixture was slowly warmed to room temperature and stirred overnight. Upon reaction completion, the mixture was quenched with 1N HCl (1 L) and extracted with EtOAc (500 mL×3). The combined organic layers were washed with water (500 mL), brine (500 mL), dried over $Na_2SO_4$, filtered and concentrated to give the title compound. $^1$H NMR (400 MHz, $CDCl_3$) δ 4.77 (m, 1H), 3.83 (m, 2H), 2.85 (m, 1H), 2.45 (m, 2H), 2.07 (m, 2H), 1.83 (m, 1H), 1.59 (d, 3H), 1.13 (d, 3H).

SCHEME B

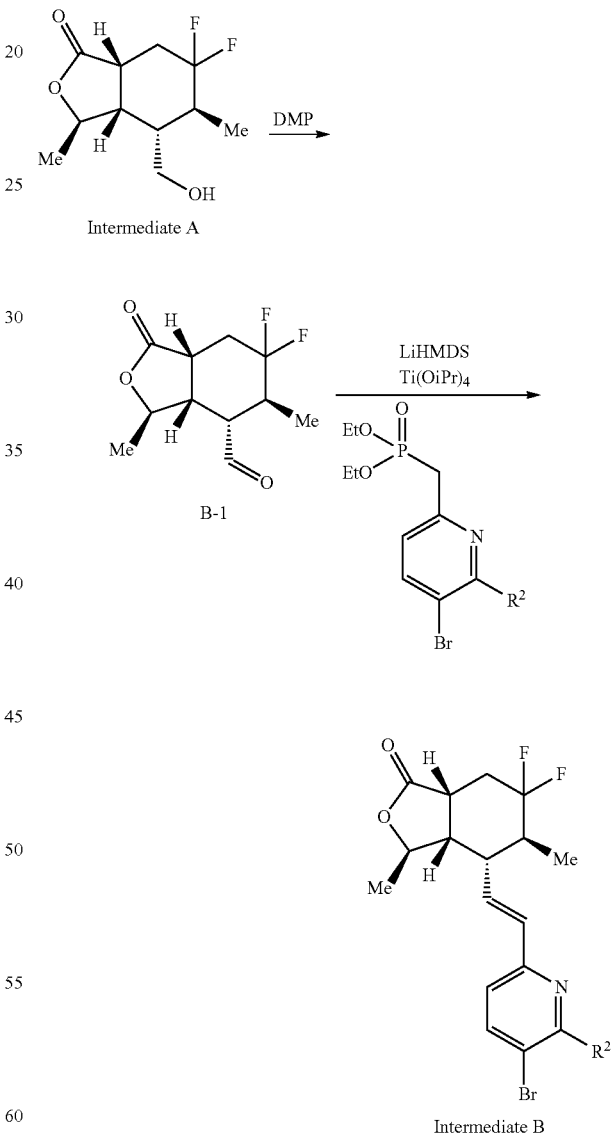

Intermediate B can be prepared according to Scheme B through a two-step process. Oxidation of intermediate A to aldehyde (B-1) and Horner-Wadsworth-Emmons olefination reaction with known or synthesized phosphonate esters provided Intermediate B.

INTERMEDIATE B1

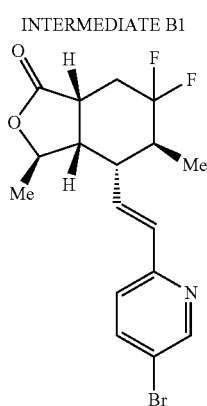 [SMILES: C[C@H]1OC(=O)[C@@H]2CC(F)(F)[C@@H](C)[C@H](/C=C/c3ccc(Br)cn3)[C@H]12]

Step 1: (3R,3aS,4R,5S,7aR)-6,6-difluoro-3,5-dimethyl-1-oxooctahydroisobenzofuran-4-carbaldehyde To a stirred solution of (3R,3aS,4R,5S,7aR)-6,6-difluoro-4-(hydroxymethyl)-3,5-dimethylhexahydroisobenzofuran-1 (3H)-one (56 g, 0.24 mol) in MeCN (600 mL) was added Dess-Martin reagent (122 g, 0.287 mol) and NaHCO$_3$ (60.3 g, 227 mol) under nitrogen at 0° C. The mixture was stirred for 4 h at 25° C. Upon reaction completion, the mixture was transferred to into L-ascorbic acid (5% aq., 1500 mL) under nitrogen, and then was filtered. The filtrate was quenched with Na$_2$SO$_3$ (5% aq., 750 mL). The solvent was removed and the product was extracted with EtOAc (750 mL×3). The combined organic layers were washed with brine (900 mL), dried over Na$_2$SO$_4$, filtered and concentrated to give the title compound, which was directly used in the next step without further purification.

Step 2: (3R,3aS,4R,5S,7aR)-4-((E)-2-(5-bromopyridin-2-yl)vinyl)-6,6-difluoro-3,5-dimethylhexahydroisobenzofuran-1 (3H)-one To a solution of diethyl ((5-bromopyridin-2-yl)methyl)phosphonate (95.6 g, 0.310 mol) in THF (400 mL) was added LiHMDS (310 mL, 0.310 mol, 1 M in THF) dropwise at 0° C. under nitrogen. The mixture was stirred for 30 min at 0° C., and then warmed up to about 25° C. Ti(OiPr)$_4$ (110 g, 0.3103 mmol) was added and the reaction was stirred for 30 min at 25° C. A solution of (3R,3aS,4R,5S,7aR)-6,6-difluoro-3,5-dimethyl-1-oxooctahydroisobenzofuran-4-carbaldehyde (36 g, 0.1552 mmol) in THF (400 mL) was added into the mixture, and stirred overnight at room temperature. Upon reaction completion, the mixture was quenched with saturated solution of potassium sodium tartrate (1 L), and then filtered. The filtrate was extracted with EtOAc (500 mL×3). The combined organic layers were washed with brine (500 mL), dried over Na$_2$SO$_4$, filtered and concentrated. The residue was purified by column chromatography with PE/EtOAc (20:1) to give the title compound. MS ESI calcd. for C$_{17}$H$_{19}$BrF$_2$NO$_2$ [M+H]$^+$ 386/388. found 386/388. $^1$H NMR (500 MHz, CDCl$_3$) δ 8.61 (d, 1H, J=2 Hz), 7.78 (dd, 1H, J=2.4, 8.4 Hz), 7.09 (d, 1H, J=8.4 Hz), 6.55 (m, 2H), 4.74 (m, 1H), 2.95 (m, 1H), 2.73 (m, 1H), 2.38-2.53 (m, 2H), 1.83-2.04 (m, 2H), 1.45 (d, 3H, J=6 Hz), 1.07 (d, 3H, J=6.8 Hz).

The following compound in Table 1 was prepared according to Scheme B using the procedure outlined in the synthesis intermediate B 1 using known or synthesized phosphonate esters.

TABLE 1

| Intermediate | Structure | IUPAC Name | Exact Mass [M + H]+ |
|---|---|---|---|
| B2 | 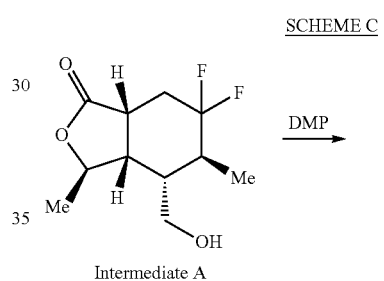 | 3R,3aS,4R,5S,7aR)-4-((E)-2-(5-bromo-6-methylpyridin-2-yl)vinyl)-6,6-difluoro-3,5-dimethylhexahydroisobenzofuran-1(3H)-one | 400/402 |

SCHEME C

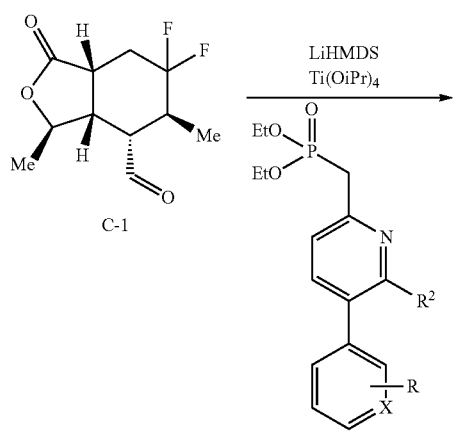

-continued

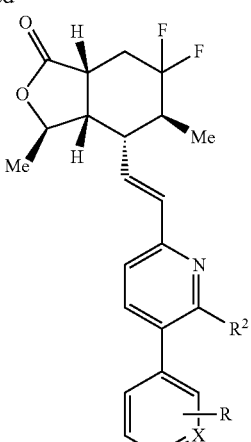

Intermediate C where R = CN, F, Me, OMe
X = C or N

Intermediate C can be prepared according to Scheme C through an oxidation to aldehyde C-1 and a Horner-Wadsworth-Emmons olefination reaction using known or synthesized phosphonate esters from Intermediate A.

INTERMEDIATE C1

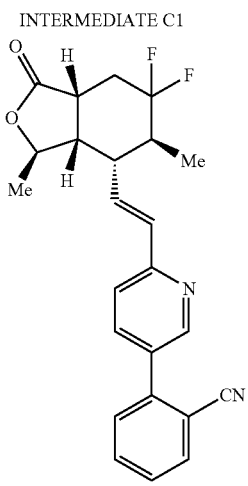 [SMILES: C[C@H]1OC(=O)[C@@H]2CC(F)(F)[C@@H](C)[C@H](/C=C/c3ccc(-c4ccccc4C#N)cn3)[C@H]12]

Step 1: (3R,3aS,4R,5S,7aR)-6,6-difluoro-3,5-dimethyl-1-oxooctahydroisobenzofuran-4-carbaldehyde To a solution of (3R,3aS,4R,5S,7aR)-6,6-difluoro-4-(hydroxymethyl)-3,5-dimethylhexahydroisobenzofuran-1(3H)-one (3.21 g, 13.70 mmol) in $CH_2Cl_2$ (100 mL) stirred at 0° C. under nitrogen was added DMP (8.72 g, 20.56 mmol). The reaction mixture was stirred for 2 h. Upon reaction completion, the mixture was quenched with $NaHCO_3$ (5% aq., 200 mL) and $Na_2SO_3$ (5% aq., 200 mL) and extracted with $CH_2Cl_2$ (3×150 mL). The combined organic layers were washed with brine (80 mL), dried over anhyd. $Na_2SO_4$ and concentrated under reduced pressure to afford the title compound. MS ESI calcd. for $C_{11}H_{15}F_2O_3$ $[M+H]^+$ 233. found 233.

Step 2: 2-(6-((E)-2-((3R,3aS,4R,5S,7aR)-6,6-difluoro-3,5-dimethyl-1-oxooctahydroisobenzofuran-4-yl)vinyl)pyridin-3-yl)benzonitrile To a solution of diethyl ((5-(2-cyanophenyl)pyridin-2-yl)methyl)phosphonate (1.98 g, 6.0 mmol) in THF (10 mL) at 0° C. was added lithium bis(trimethylsilyl)amide (6.0 mL, 6.0 mmol, 1 M in THF). The reaction was stirred for 30 minutes at 0° C. before allowing it to warm to RT. Titanium (IV) isopropoxide (1.76 mL, 6.0 mmol) was added to the reaction mixture. The reaction mixture was stirred for 5 min., then a solution of (3R,3aS,4R,5S,7aR)-6,6-difluoro-3,5-dimethyl-1-oxooctahydroisobenzofuran-4-carbaldehyde (0.697 g, 3.0 mmol) in THF (10 mL) was added and stirred at RT for 1 hour. The reaction was quenched with aqueous sat. potassium sodium tartrate and the product was extracted with EtOAc. The organic phase was dried with $Na_2SO_4$, concentrated and purified by silica gel chromatography (0-40% EtOAc in hexanes) to provide 2-(6-((E)-2-((3R,3aS,4R,5S,7aR)-6,6-difluoro-3,5-dimethyl-1-oxooctahydroisobenzofuran-4-yl)vinyl)pyridin-3-yl)benzonitrile. MS ESI calcd. for $C_{24}H_{23}F_2N_2O_2[M+H]^+$ 409. found 409. $^1H$ NMR (500 MHz, $CDCl_3$) δ 8.75 (d, J=2.3 Hz, 1H); 7.97 (d, J=8.0 Hz, 1H); 7.86 (d, J=7.8 Hz, 1H); 7.75 (t, J=7.7 Hz, 1H); 7.56 (t, J=7.7 Hz, 2H); 7.37 (d, J=8.1 Hz, 1H); 6.69-6.71 (m, 2H); 4.80 (m, 1H); 2.97-3.02 (m, 1H); 2.79-2.84 (m, 1H); 2.53-2.60 (m, 1H); 2.41-2.49 (m, 1H); 2.02-2.16 (m, 1H); 1.85-1.99 (m, 1H); 1.53 (d, J=6.0 Hz, 3H), 1.13 (d, J=6.6 Hz, 3H).

The following compound in Table 2 was prepared according to Scheme C using the procedure outlined in the synthesis intermediate C1 using known or synthesized phosphonate esters.

TABLE 2

| Intermediate | Structure | IUPAC Name | Exact Mass [M + H]+ |
|---|---|---|---|
| C2 | 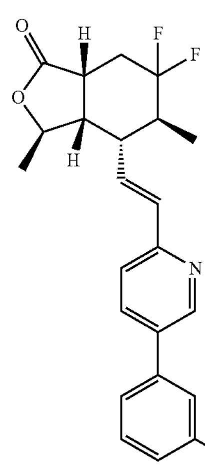 | (3R,3aS,4R,5S,7aR)-6,6-difluoro-4-((E)-2-(5-(3-fluorophenyl)pyridin-2-yl)vinyl)-3,5-dimethylhexahydroisobenzofuran-1(3H)-one | 402 |

SCHEME D

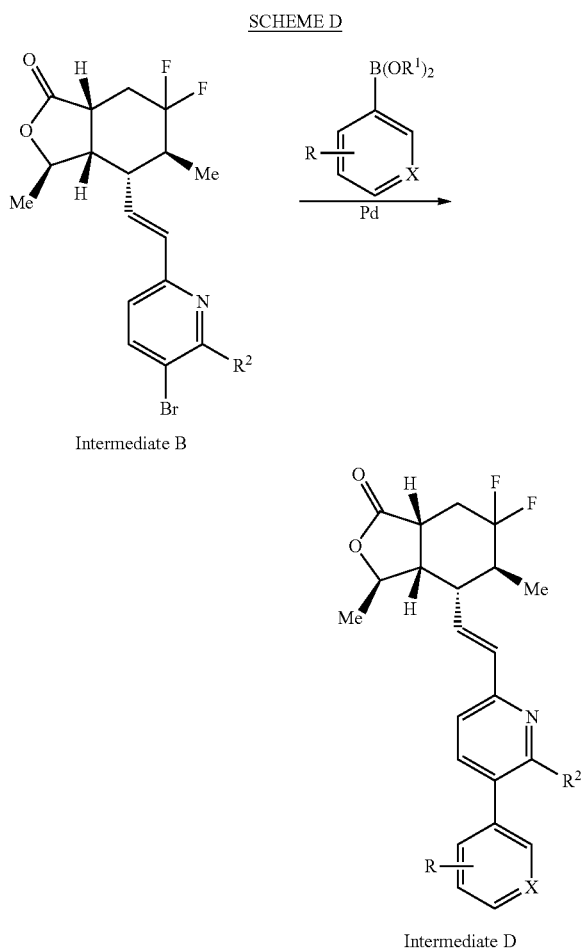

where R¹ = H or alkyl;
R = F, CN, Me, OMe; and
X = C or N

Intermediate D can be prepared via reaction of known or commercially available aryl/heteroaryl boronic acids or esters with Intermediate B, according to Scheme D.

INTERMEDIATE D1

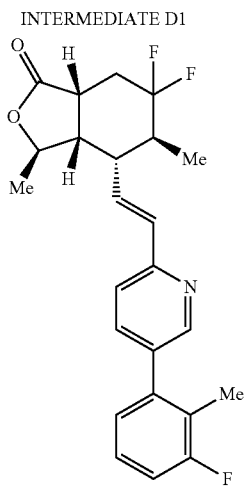 [SMILES: Cc1c(F)cccc1-c1ccc(/C=C/[C@@H]2[C@@H]3[C@@H](C)OC(=O)[C@@H]3CC(F)(F)[C@H]2C)nc1]

To a mixture of (3R,3aS,4R,5S,7aR)-4-((E)-2-(5-bromopyridin-2-yl)vinyl)-6,6-difluoro-3,5-dimethylhexahydroisobenzofuran-1(3H)-one (0.463 g, 1.2 mmol), (3-fluoro-2-methylphenyl)boronic acid (0.240 g, 1.560 mmol) and potassium phosphate tribasic (1.80 mL, 3.60 mmol, 2 M in water) in THF (5 mL) was added 1,1'-bis(di-tert-butylphosphino)ferrocene palladium dichloride (0.039 g, 0.060 mmol) at RT. The reaction was purged and flushed with $N_2$(g) 3 times before heating to 50° C. for 4 hours. The reaction mixture was diluted with EtOAc, and the organic was washed with water and brine. and the product was extracted with EtOAc. The organic phase was dried with $Na_2SO_4$ and was concentrated. The residue was purified by column chromatography on silica (0-30% EtOAc in hexanes) to afford (3R,3aS,4R,5S)-6,6-difluoro-4-((E)-2-(5-(3-fluoro-2-methylphenyl)pyridin-2-yl)vinyl)-3,5-dimethylhexahydroisobenzofuran-1(3H)-one. MS ESI calcd. for $C_{24}H_{25}F_3NO_2$ [M+H]⁺ 416. found 416. ¹H NMR (500 MHz, $CDCl_3$) δ 8.57 (s, 1H); 7.66 (d, J=7.6 Hz, 1H); 7.24-7.33 (m, 2H); 7.06-7.14 (m, 2H); 6.63-6.65 (m, 2H); 4.80 (dd, J=10.4, 5.8 Hz, 1H); 2.99 (dd, J=12.7, 6.9 Hz, 1H); 2.76-2.85 (m, 1H); 2.57 (dd, J=14.1, 7.5 Hz, 1H); 2.45 (s, 1H); 2.24 (s, 3H); 2.09 (d, J=13.7 Hz, 1H); 1.87-1.99 (m, 1H); 1.53 (d, J=14 Hz, 3H); 1.14 (d, J=6.4 Hz, 3H).

1e;3qThe following compounds in Table 3 were prepared according to Scheme D using the procedure outlined in the synthesis intermediate D1 using known or commercially available aryl/heteroaryl boronic acids or esters.

TABLE 3

| Intermediate | Structure | IUPAC Name | Exact Mass [M + H]+ |
|---|---|---|---|
| D2 | (structure shown) | (3R,3aS,4R,5S,7aR)-6,6-difluoro-4-((E)-2-(5-(2-fluoro-3-methylphenyl)pyridin-2-yl)vinyl)-3,5-dimethylhexahydroisobenzofuran-1(3H)-one | 416 |

TABLE 3-continued

| Inter-mediate | Structure | IUPAC Name | Exact Mass [M + H]+ |
|---|---|---|---|
| D3 | 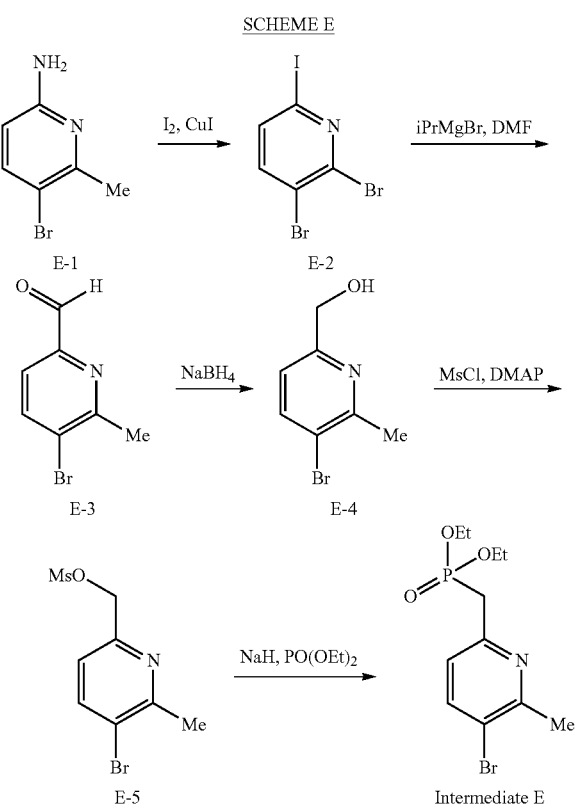 | 2-(6-((E)-2-((3R,3aS,4R,5S,7aR)-6,6-difluoro-3,5-dimethyl-1-oxooctahydro-isobenzofuran-4-yl)vinyl)-2-methylpyridin-3-yl)benzonitrile | 423 |

SCHEME E

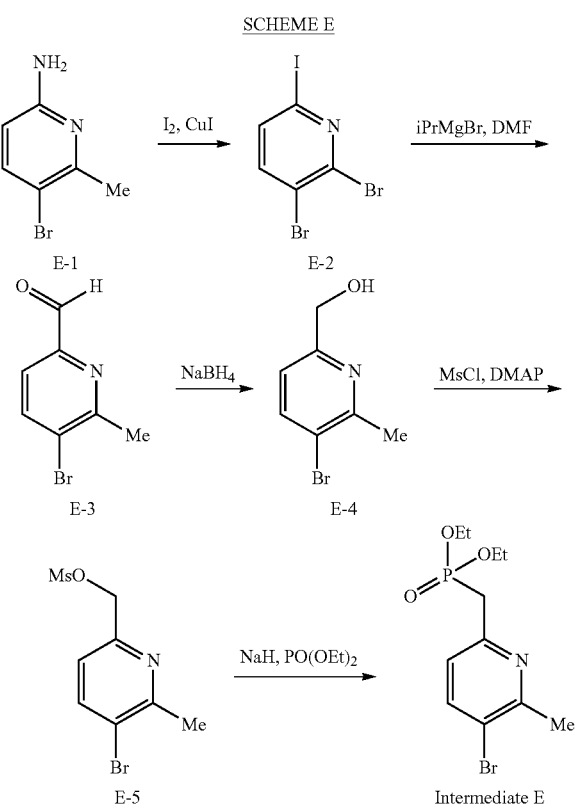

Intermediate E can be prepared from commercially available 5-bromo-6-methylpyridin-2-amine (E-1) according to Scheme E. A Sandmeyer reaction provided iodide (E-2) which was subsequently followed by metal-halogen exchange and formylation by DMF to yield aldehyde (E-3). Reduction of (E-3) furnished the corresponding alcohol (E-4) which was mesylated to yield (E-5). Finally, displacement by diethyl phosphonate yielded Intermediate E.

INTERMEDIATE E

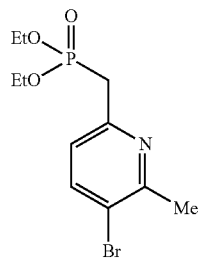

Step 1: 3-bromo-6-iodo-2-methylpyridine

To a solution of 5-bromo-6-methylpyridin-2-amine (20.0 g, 0.107 mol) in DCM (300 mL) was added CuI (20.4 g, 0.107 mol) and $I_2$ (27.1 g, 0.321 mol) at rt. The mixture was stirred and isoamyl nitrite (37.6 g, 0.321 mol) was added at 65° C. The resulting mixture was stirred at this temperature for 30 min. After cooling, the mixture was adsorbed on silica gel to afford the title compound.

Step 2: 5-bromo-6-methylpicolinaldehyde

To a solution of 3-bromo-6-iodo-2-methylpyridine (100 g, 0.336 mol) in THF (1 L) was added i-PrMgCl (201 mL, 0.402 mol) at −15° C. The mixture was stirred at −15° C. for 1 hour. DMF (37 g, 0.503 mol) was added dropwise and the temperature was maintained below 0° C. After warming to RT over 1 hour, the reaction was cooled to −15° C. before 200 mL of HCl (2 mol/L) was added. The product was extracted with EtOAc and the organic layer was washed with brine, dried over $Na_2SO_4$, filtered and concentrated to yield the title compound, which was carried forward without further purification.

Step 3: (5-bromo-6-methylpyridin-2-yl)methanol

A mixture of 5-bromo-6-methylpicolinaldehyde (25 g, 0.125 mol) was dissolved in THF (100 mL) and MeOH (100 mL) cooled in an ice bath. $NaBH_4$ (7.10 g, 0.187 mol) was added and stirred below 20° C. for 2 hours. After cooled to 0° C., $H_2O$ (50 mL) was added, and the resulting mixture was extracted with EtOAc. The organic layer was washed with brine, dried over $Na_2SO_4$, filtered and concentrated to obtained crude product which was purified by silica gel chromatography (EtOAc in petroleum ether, 0-50%) to give the title compound.

Step 4: (5-bromo-6-methylpyridin-2-yl)methyl methanesulfonate

To a solution of (5-bromo-6-methylpyridin-2-yl)methanol (100 g, 0.495 mol) in DCM (1 L) was added DIEA (191 g, 1.5 mol) and DMAP (8.0 g, 65 mmol) below 0° C. MsCl (68.3 g, 0.594 mol) was added dropwise. The resulting mixture was stirred at this temperature for 30 min. $H_2O$ (2 L) was added, and the resulting mixture was extracted with $CH_2Cl_2$. The organic layer was washed with brine, dried over $Na_2SO_4$, filtered and concentrated to give the crude residue which was purified by silica gel chromatography (EtOAc in petroleum ether, 0-10%) to obtain the title compound.

Step 5: diethyl ((5-bromo-6-methylpyridin-2-yl)methyl)phosphonate

A mixture of diethoxyphosphino-1-one (118 g, 0.860 mol) dissolved in DMF (1.5 L) was cooled to 0° C. NaH (60% wt in mineral oil, 42.5 g, 1.06 mol) was added slowly and the reaction was stirred at 0° C. for 30 min. (5-Bromo-6-methylpyridin-2-yl)methyl methanesulfonate (200 g, 0.71 mol) dissolved in DMF (500 mL) was added at −5° C. The resulting mixture was stirred at this temperature for 2 hours. After cooling, the mixture was poured into ice water, the resulting mixture was extracted with EtOAc. The organic layer was washed with brine, dried over $Na_2SO_4$, filtered and concentrated. The residue was purified by silica gel chromatography (EtOAc in petroleum ether, 0-30%) to afford the title compound. MS ESI calcd. for $C_{11}H_{18}BrNO_3P$ $[M+H]^+$ 322/324. found 322/324. $^1H$ NMR (300 MHz, DMSO-$d_6$) δ 7.95 (d, J=8.1 Hz, 1H), 7.11-7.15 (m, 1H), 3.94-4.04 (m, 4H), 3.34-3.42 (m, 2H), 2.54 (s, 3H), 1.16-1.21 (m, 6H).

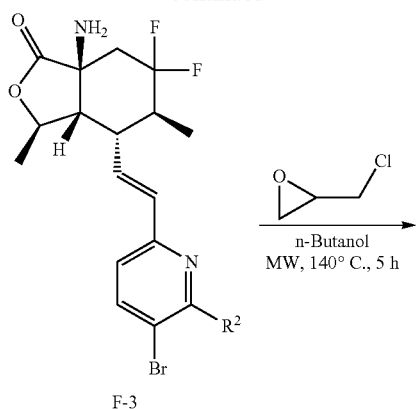

SCHEME F

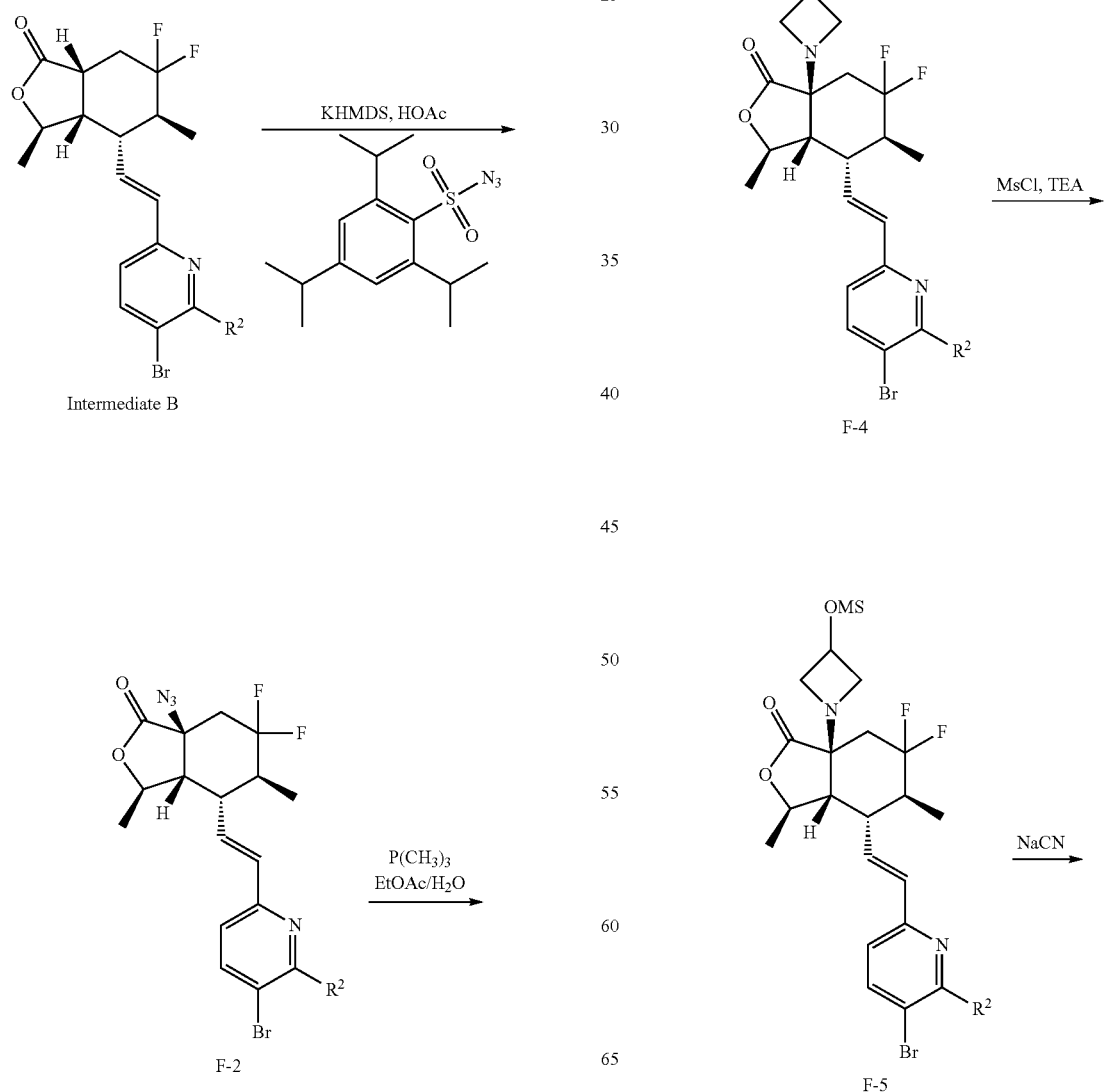

-continued

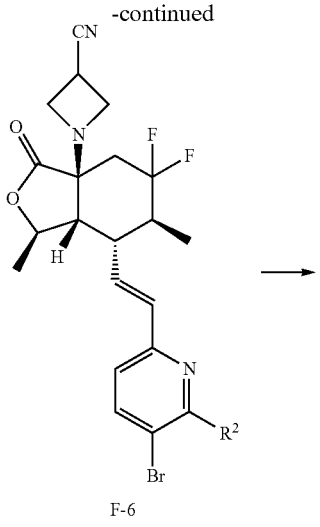

F-6

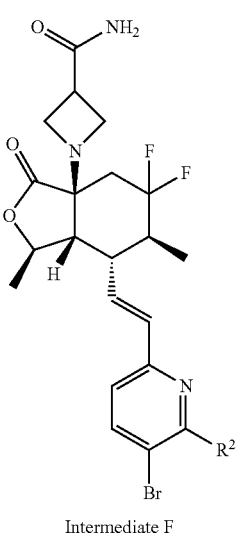

Intermediate F

Intermediate F can be prepared from Intermediate B with the introduction of azide under anionic conditions to yield azide (F-2) according to scheme F. A Staudinger reaction provided amine (F-3) which is subsequently reacted with 2-(chloromethyl)oxirane to yield azetidine (F-4). Mesylation of alcohol (F-4) yielded mesylate (F-5) which was displaced by sodium cyanide to form nitrile adduct (F-6). Hydrolysis of nitrile (F-6) afforded intermediate F.

INTERMEDIATE F

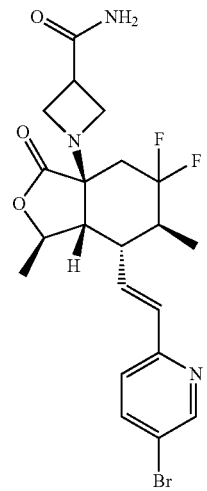

Step 1: (3R,3aS,4R,5 S,7aS,E)-7a-azido-4-(2-(5-bromopyridin-2-yl)vinyl)-6,6-difluoro-3,5-dimethyl-hexahydroisobenzofuran-1(3H)-one To a solution of (3R,3aS,4R,5S,7aR,E)-4-(2-(5-bromopyridin-2-yl)vinyl)-6,6-difluoro-3,5-dimethyl-hexahydroisobenzofuran-1(3H)-one (4.3 g, 11.13 mmol) in dry, de-oxygenated THF (40 mL) at 0° C. was added KHMDS (0.5 M in THF, 33.4 mL, 16.70 mmol) dropwise. The reaction was stirred at 0° C. for 15 minutes and then cooled to −78° C. A pre-cooled, de-gassed solution of 2,4,6-triisopropylbenzenesulfonyl azide (6.89 g, 22.27 mmol) in THF (15 mL) was added and the mixture was stirred at −78° C. over 15 min. AcOH (1.912 mL, 33.4 mmol) was then added at −78° C. and the reaction mixture was warmed to 40° C. and stirred at this temperature for 1 h. The mixture was cooled to room temperature, diluted with EtOAc (300 mL), washed with aqueous sodium hydrogen carbonate (saturated, 100 mL), dried (anhydrous $Na_2SO_4$), filtered and the solvent was evaporated under reduced pressure. The residue was purified by column chromatography on a silica gel with (EtOAc/hexane=1/6) to give the title compound. MS ESI calcd. for $C_{17}H_{18}BrF_2N_4O_2$ $[M+H]^+$ 427. found 427.

Step 2: (3R,3aS,4R,5S,7aS,E)-7a-amino-4-(2-(5-bromopyridin-2-yl)vinyl)-6,6-difluoro-3,5-dimethyl-hexahydroisobenzofuran-1(3H)-one To a solution of (3R,3aS,4R,5S,7aS,E)-7a-azido-4-(2-(5-bromopyridin-2-yl)vinyl)-6,6-difluoro-3,5-dimethyl-hexahydroisobenzofuran-1 (3H)-one (4.4 g, 10.30 mmol) in EtOAc (60 mL) was added with $P(CH_3)_3$(1M in THF, 15.45 mL, 15.45 mmol) and $H_2O$ (5.57 mL, 309 mmol) at room temperature. The reaction mixture was stirred overnight at room temperature. The excess solvent was removed under reduced pressure and the residue was purified by column chromatography on a silica gel with (EtOAc/hexane=1/2) to give the title compound. MS ESI calcd. for $C_{17}H_{20}BrF_2N_2O_2$ $[M+H]^+$ 401. found 401.

Step 3: (3R,3aS,4R,5S,7aS,E)-4-(2-(5-bromopyridin-2-yl)vinyl)-6,6-difluoro-7a-(3-hydroxyazetidin-1-yl)-3,5-dimethyl-hexahydroisobenzofuran-1(3H)-one A mixture of (3R,3aS,4R,5 S,7aS,E)-7a-amino-4-(2-(5-bromopyridin-2-yl)vinyl)-6,6-difluoro-3,5-dimethyl-hexahydroisobenzofuran-1(3H)-one (600 mg, 1.5 mmol), 2-(chloromethyl)oxirane (2.76 g, 30 mmol) in n-Butanol (5 mL) was stirred at 140° C. in Discover SP microwave for 5 h. The reaction mixture was cooled to rt and purified by HPLC (MeCN/water with 0.01% TFA modifier) to give the title compound. MS ESI calcd. for $C_{20}H_{24}BrF_2N_2O_3$ [M+H]$^+$ 457. found 457.

Step 4: 1-((1R,3aS,6S,7R,7aS)-7-((E)-2-(5-bromopyridin-2-yl)vinyl)-5,5-difluoro-1,6-dimethyl-3-oxo-octahydroisobenzofuran-3a-yl)azetidin-3-yl methanesulfonate To a solution of (3R,3aS,4R,5S,7aS,E)-4-(2-(5-bromopyridin-2-yl)vinyl)-6, 6-difluoro-7a-(3-hydroxyazetidin-1-yl)-3,5-dimethyl-hexahydroisobenzofuran-1(3H)-one (240 mg, 0.53 mmol) in $CH_2Cl_2$ (10 mL) at 0° C. was added $Et_3N$ (107 mg, 1.06 mmol) and MsCl (121 mg, 1.06 mmol). The mixture was then stirred at room temperature for 2 h. The mixture was quenched with water (1 mL) and the organic phase was washed with brine (5 mL), dried over anhydrous $Na_2SO_4$, filtered and concentrated to give the title compound. MS ESI calcd. for $C_{21}H_{26}BrF_2N_2O_5S$ [M+H]$^+$ 535. found 535.

Step 5: 1-((1R,3aS,6S,7R,7aS)-7-((E)-2-(5-bromopyridin-2-yl)vinyl)-5,5-difluoro-1,6-dimethyl-3-oxo-octahydroisobenzofuran-3a-yl)azetidine-3-carbonitrile A mixture of 1-((1R,3aS,6S,7R,7aS)-7-((E)-2-(5-bromopyridin-2-yl)vinyl)-5,5-difluoro-1,6-dimethyl-3-oxo-octahydroisobenzofuran-3a-yl)azetidin-3-yl methanesulfonate (120 mg, 0.224 mmol) and cyano sodium (60 mg, 1.22 mmol) in DMF (2 mL) and water (0.5 mL) was stirred at 100° C. for 12 h, then cooled to rt. EtOAc (100 mL) was added to the mixture. The mixture was washed with water (10 mL×3) and brine (10 mL). The organic layer was dried over $Na_2SO_4$, filtered and concentrated. The residue was purified with prep-TLC (hexane/EtOAc=1/1) to afford the title compound. MS ESI calcd. for $C_{21}H_{23}BrF_2N_3O_2$ [M+H]$^+$ 466. found 466.

Step 6: 1-((1R,3aS,6S,7R,7aS)-7-((E)-2-(5-bromopyridin-2-yl)vinyl)-5,5-difluoro-1,6-dimethyl-3-oxo-octahydroisobenzofuran-3a-yl)azetidine-3-carboxamide To a solution of 1-((1R,3aS,6S,7R,7aS)-7-((E)-2-(5-bromopyridin-2-yl)vinyl)-5,5-difluoro-1,6-dimethyl-3-oxo-octahydroisobenzofuran-3a-yl)azetidine-3-carbonitrile (32 mg, 0.062 mmol) in DMSO (2 mL) at room temperature was added potassium carbonate (30 mg, 0.218 mmol) and hydrogen peroxide (30%, 80 mg, 0.706 mmol). The mixture was stirred for 12 h at room temperature. The reaction mixture was purified with flash chromatograph ($CH_3CN/H_2O$ (0.01% TFA)) directly to afford the title compound. MS ESI calcd. for $C_{21}H_{25}BrF_2N_3O_3$ [M+H]$^+$ 486. found 486.

General Synthetic Schemes

Representative compounds of the present invention can be synthesized according to the general schemes outlined below as well as the representative examples that follow. The schemes are illustrative in nature and the invention should not be construed as being limited by the chemical reactions and conditions expressed herein. The preparation of the various starting materials used in the schemes is well with the skill level of a practitioner of this art. Unless otherwise indicated, the definition for a variable is the same as that provided in Formula I.

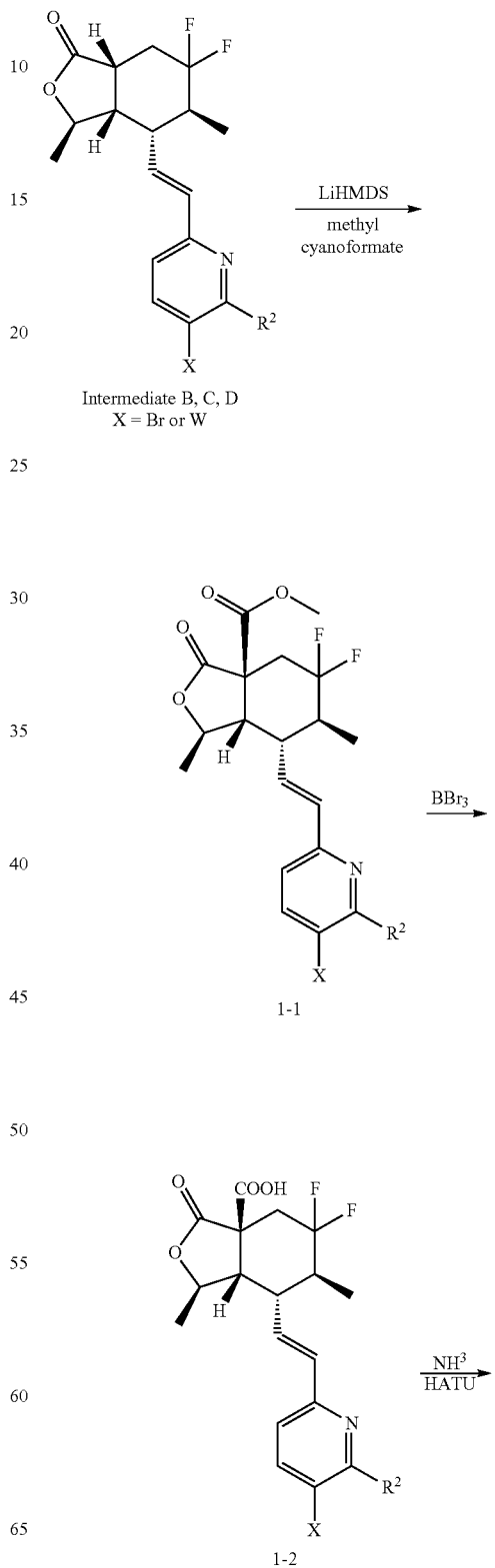

SCHEME 1

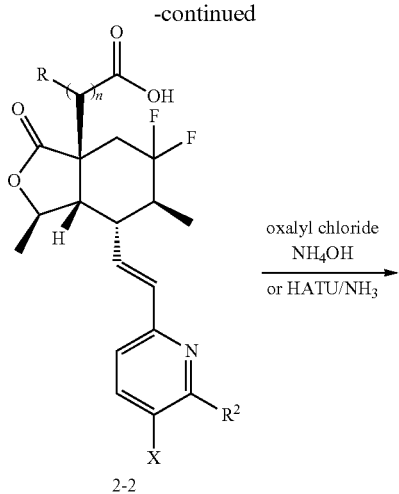

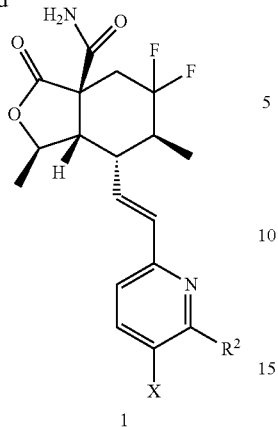

Compounds of Formula (1) can prepared via modification of intermediate B, C or D by generating the corresponding anion using bases such as LiHMDS and reaction with an appropriate electrophile to yield (1-1). Subsequent hydrolysis and reaction with the resultant carboxylic acids (1-2) via amide coupling conditions with ammonia provided compounds of Formula (1).

SCHEME 2

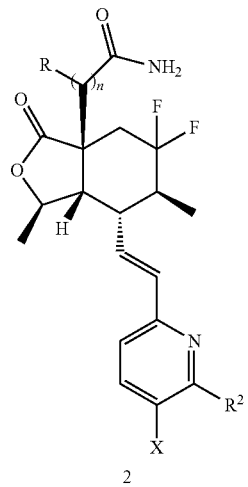

Compounds of Formula (2) can be prepared from intermediate B, C or D via enolate formation and reaction with an appropriate electrophile to yield (2-1). Hydrolysis to carboxylic acid (2-2) enabled formation of the corresponding acid chloride which upon exposure to ammonium hydroxide provided compounds of Formula (2). Alternatively, coupling conditions with ammonia provided compounds of Formula (2).

SCHEME 3

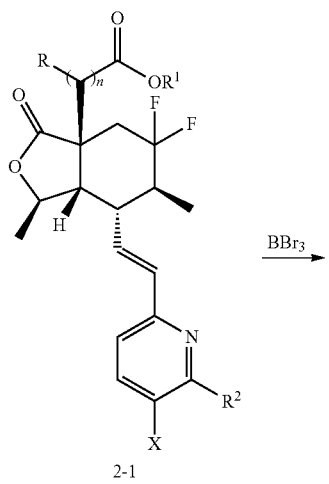

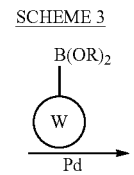

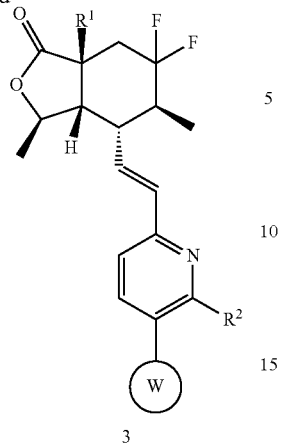
3
where R is H or alkyl
Compounds of Formula (3) can prepared from intermediates generated using Scheme 1 from intermediate B or intermediate F. A palladium-mediated Suzuki coupling reaction of bromide (3-1) with known or commercially available boronic acids or esters furnished compounds of the Formula (3).
SCHEME 4
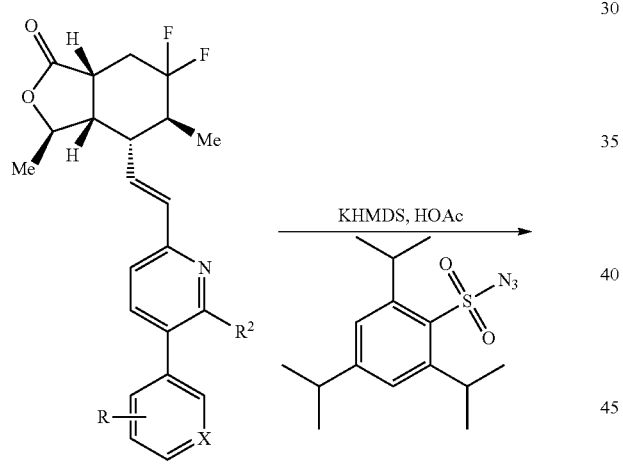
intermediate C
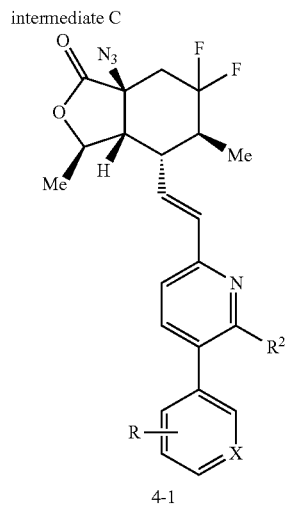
4-1
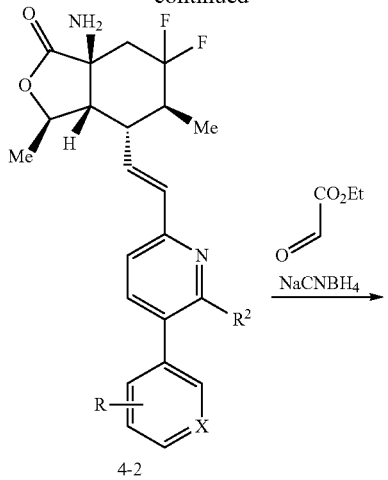
4-2
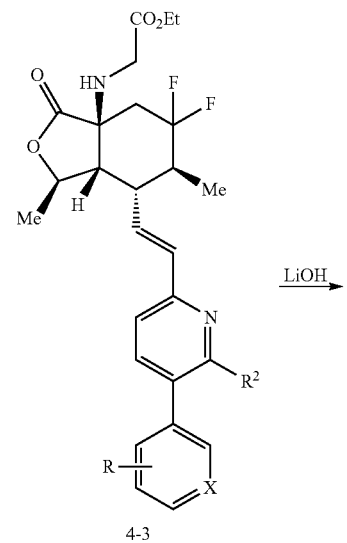
4-3
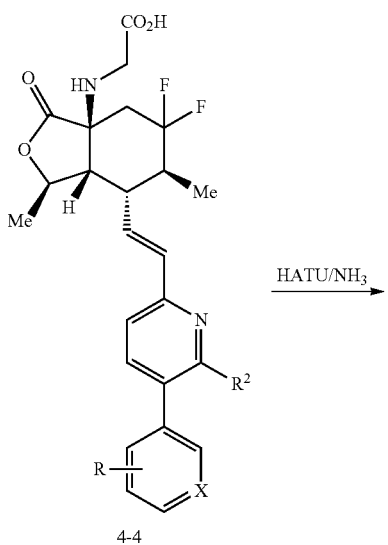
4-4

-continued

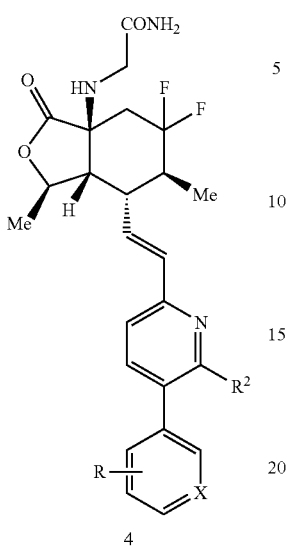

4 where R = CN, F, Me, OMe; and X = C or N

Compounds of Formula (4) can be prepared from intermediates generated from Intermediate C according to Scheme 4. Introduction of azide under anionic conditions yields azide (4-1) and a Staudinger reaction provided the corresponding amine (4-2). Reductive amination installed the pendent ester to form adduct (4-3). Saponification to acid (4-4) and amide coupling conditions with ammonia furnished compounds of the Formula (4).

SCHEME 5

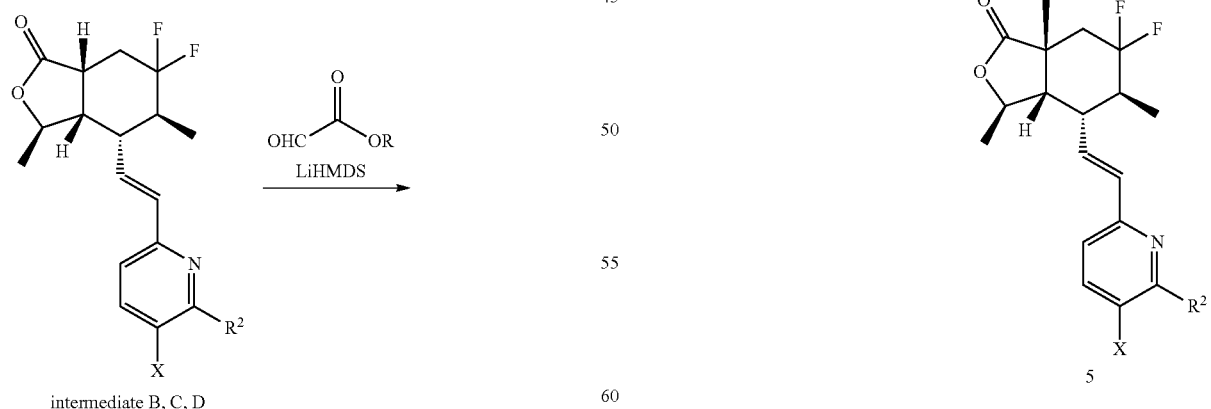

intermediate B, C, D

X = Br or W
R = H or alkyl;
$R^a$ = H or alkyl

-continued

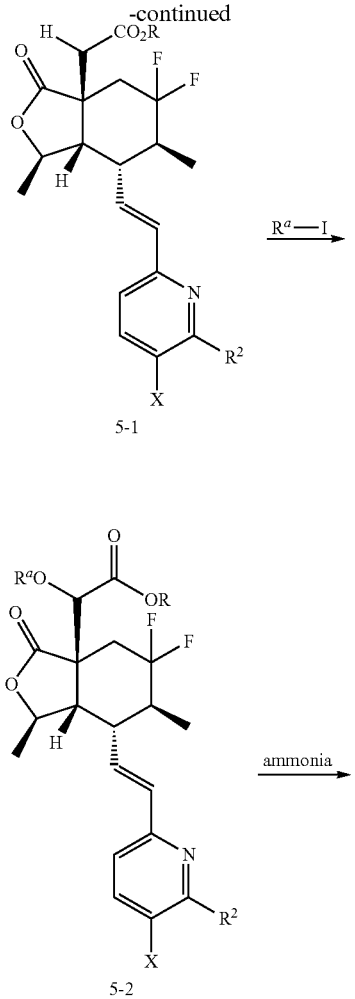

5-1

5-2

5

Compounds of Formula (5) can be prepared from intermediates generated from intermediate B, C, or D according to Scheme 5. Enolate formation and reaction with glyoxalate provided alcohol (5-1). The alcohol (5-1) can be alkylated to form an ether (5-2) or carried forward directly to compounds of the Formula (5).

SCHEME 6

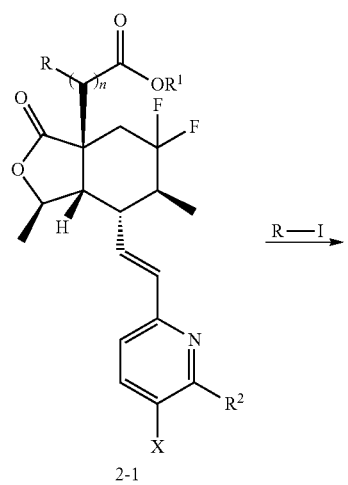

2-1

X = Br or W
R = R$^b$
R$^1$ = alkyl
n = 1-4

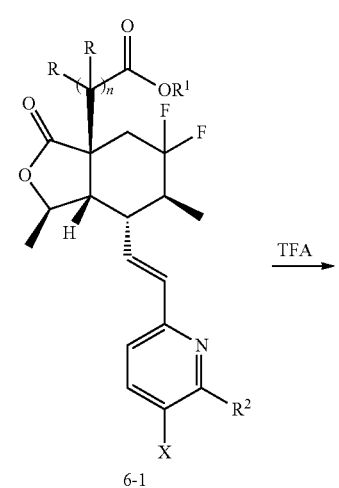

6-1

TFA →

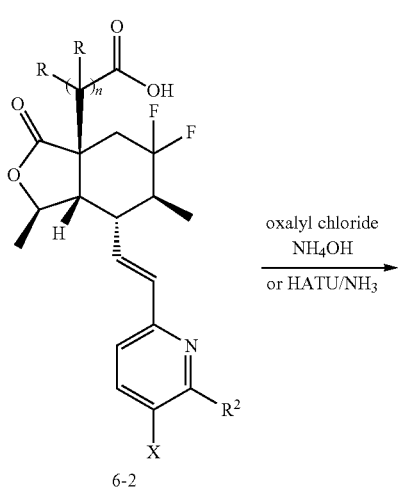

6-2 oxalyl chloride
NH$_4$OH
or HATU/NH$_3$
→

-continued

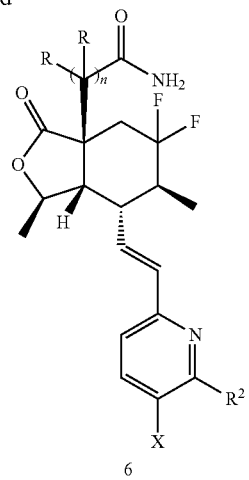

6

Compounds of Formula (6) can be prepared from intermediate (2-1) generated from Scheme 2. Enolate formation and alkylation with an alkyl halide provided adduct (6-1). Hydrolysis to acid (6-2) and subsequent formation of the corresponding acid chloride, which upon exposure to ammonium hydroxide, provided compounds (6). Alternatively, coupling conditions with ammonia provided compound s (6).

EXAMPLES

The following schemes and examples are provided so that the invention will be more fully appreciated and understood. Starting materials are made using known procedures or as illustrated below.

Example 1

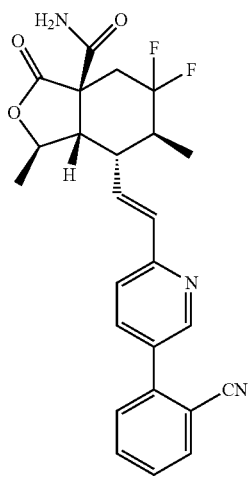 [SMILES: C[C@H]1OC(=O)[C@]2(C(N)=O)CC(F)(F)[C@@H](C)[C@H](/C=C/c3ccc(-c4ccccc4C#N)cn3)[C@H]12]

Step 1: (1R,3aR,6S,7R,7aS)-7-((E)-2-(5-(2-cyanophenyl)pyridin-2-yl)vinyl)-5, 5-difluoro-1,6-dimethyl-3-oxooctahydroisobenzofuran-3a-carboxamide To 2-(6-((E)-2-((3R,3aS,4R,5S,7aR)-6,6-difluoro-3,5-dimethyl-1-oxooctahydroisobenzofuran-4-yl)vinyl)pyridin-3- yl)benzonitrile (0.66 g, 1.62 mmol) in 2-Me-THF (5 mL) at 0° C. under $N_2$(g) was added lithium bis(trimethylsilyl)amide (0.34 g, 2.02 mmol, 1 M in THF). The reaction mixture was stirred at 0° C. for 30 min before cooling the system to −78° C., and adding methyl cyanoformate (0.18 g, 2.10 mmol). After stirring for 40 min at −78° C., the reaction mixture was allowed to warm to RT and was stirred for 20 min. The reaction mixture was cooled to 0° C., quenched with sat. $NH_4Cl_{(aq)}$, and the product was extracted with EtOAc. The organic phase was washed with brine, dried with $Na_2SO_4$, and was concentrated. The residue was purified by column chromatography on silica (0-40% EtOAc in hexanes) to afford the title compound. MS ESI calcd. for $C_{26}H_{25}F_2N_2O_4[M+H]^+$ 467. found 467.

Step 2: (1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-carboxylic acid To a solution of (1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-carboxamide (560 mg, 1.20 mmol) in DCM (5 mL), boron tribromide (4.80 mL, 4.80 mmol, 1 M) was added at 0° C. under $N_2$(g). After stirring at 0° C. for 30 min, the reaction mixture was allowed to warm to RT and stirred for 30 min. Upon completion of the reaction, the system was cooled to 0° C. and was quenched with sat. $NH_4Cl_{(aq)}$. The product was extracted with EtOAc and the organic phase was dried with $Na_2SO_4$ before concentrating. The residue was purified by column chromatography on silica (5% MeOH in DCM) to provide the title compound. MS ESI calcd. for $C_{25}H_{23}F_2N_2O_4[M+H]^+$ 453. found 453. $^1$H NMR (500 MHz, $CDCl_3$) δ 9.00 (s, 1H); 8.19-8.33 (m, 1H); 7.89 (d, J=7.5 Hz, 1H); 7.69-7.83 (m, 2H); 7.59-7.69 (m, 2H); 6.92 (d, J=15.9 Hz, 1H); 6.56-6.74 (br s, 1H); 4.75-4.82 (m, 1H); 3.15-3.31 (m, 2H); 2.97-3.09 (m, 1H); 2.13 (dd, J=35.5, 15.5 Hz, 2H); 1.58 (d, J=5.9, 3 H); 1.15 (d, J=6.6 Hz, 3H).

Step 3: (1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-carboxamide HATU (0.43 g, 1.13 mmol) was added to a solution of (1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-carboxylic acid (0.34 g, 0.75 mmol) in DMF (2 mL). The solution was stirred at 25° C. for 5 min, before ammonia (6.01 mL, 3.01 mmol) was added to the reaction mixture. After 1 hour at 25° C., the reaction mixture was diluted with EtOAc and the organic was washed with water and brine. The organic phase was dried with $Na_2SO_4$, concentrated, and was purified by reverse phase HPLC (acetonitrile/water with 0.1% TFA modifier) to provide the product as a TFA salt. The TFA salt was diluted with EtOAc, washed with sat. $NaHCO_{3(aq)}$, dried with $Na_2SO_4$, and concentrated to provide the title compound. MS ESI calcd. for $C_{25}H_{24}F_2N_3O_3[M+H]^+$ 452. found 452. $^1$H NMR (500 MHz, $CDCl_3$) δ 8.76 (d, J=2.65 Hz, 1H); 7.96 (dd, J=8.0, 2.6 Hz, 1H); 7.86 (d, J=7.7 Hz, 1H); 7.75 (t, J=7.5 Hz, 1H); 7.56 (t, J=7.9 Hz, 2H); 7.36 (d, J=8.0 Hz, 1H); 6.69-6.72 (m, 2H); 4.69-4.80 (m, 1H); 3.38-3.49 (m, 1H); 3.13-3.22 (m, 1H); 2.65-2.77 (m, 1H); 2.21 (s, 3H); 2.04-2.25 (m, 1H); 1.58 (d, J=5.95, 2.98 Hz, 3H); 1.09 (d, J=6.5 Hz, 3H). PAR-1 FLIPR $IC_{50}$=2.93 nM.

The following examples in Table 4 were prepared according to Scheme 1 using the procedure outlined in the synthesis of Example 1. Intermediate C or D may be used in step 1.

TABLE 4

| Ex | Structure | IUPAC Name | Exact Mass [M + H]+ | PAR-1 FLIPR IC$_{50}$ (nM) |
| --- | --- | --- | --- | --- |
| 2 | 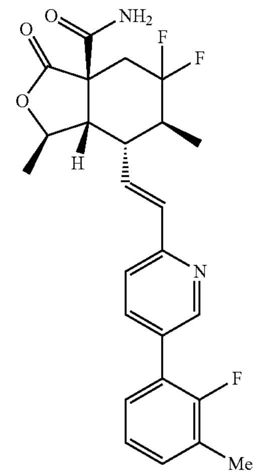 [SMILES: Cc1cccc(-c2ccc(/C=C/[C@@H]3[C@@H]4[C@@H](C)OC(=O)[C@]4(C(N)=O)CC(F)(F)[C@H]3C)nc2)c1F] | (1R,3aR,6S,7R,7aS)-5,5-difluoro-7-((E)-2-(5-(2-fluoro-3-methylphenyl)pyridin-2-yl)vinyl)-1,6-dimethyl-3-oxooctahydroisobenzofuran-3a-carboxamide | 459 | 3.8 |
| 3 | 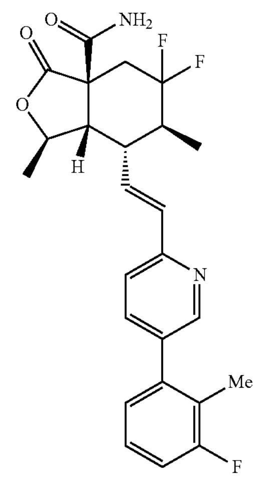 [SMILES: Cc1c(F)cccc1-c1ccc(/C=C/[C@@H]2[C@@H]3[C@@H](C)OC(=O)[C@]3(C(N)=O)CC(F)(F)[C@H]2C)nc1] | (1R,3aR,6S,7R,7aS)-5,5-difluoro-7-((E)-2-(5-(3-fluoro-2-methylphenyl)pyridin-2-yl)vinyl)-1,6-dimethyl-3-oxooctahydroisobenzofuran-3a-carboxamide | 459 | 1.37 |
| 4 | 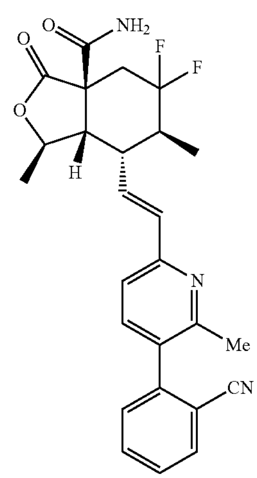 [SMILES: Cc1nc(/C=C/[C@@H]2[C@@H]3[C@@H](C)OC(=O)[C@]3(C(N)=O)CC(F)(F)[C@H]2C)ccc1-c1ccccc1C#N] | (1R,3aR,6S,7R,7aS)-7-((E)-2-(5-(2-cyanophenyl)-6-methylpyridin-2-yl)vinyl)-5,5-difluoro-1,6-dimethyl-3-oxooctahydroisobenzofuran-3a-carboxamide | 481 | 6.92 |

Example 5

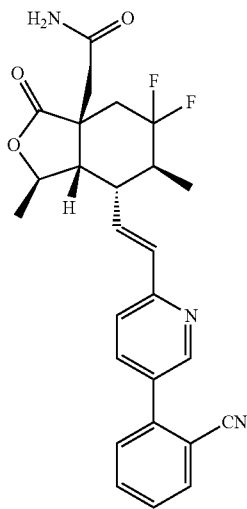 [SMILES: C[C@H]1OC(=O)[C@]2(CC(N)=O)CC(F)(F)[C@@H](C)[C@H](/C=C/c3ccc(-c4ccccc4C#N)cn3)[C@H]12]

Step 1: tert-butyl 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)acetate To a solution of 2-(6-((E)-2-((3R,3aS,4R,5S,7aR)-6,6-difluoro-3,5-dimethyl-1-oxooctahydroisobenzofuran-4-yl)vinyl)pyridin-3-yl)benzonitrile (540 mg, 1.322 mmol) in THF (5 mL) was added lithium bis(trimethylsilyl)amide (1.98 mL, 1.98 mmol, 1 M) at 0° C. After stirring for 20 minutes, the system was cooled to −78° C., and tert-butyl bromoacetate (516 mg, 2.64 mmol) was added. After stirring at −78° C. for 30 minutes, the reaction was warmed to RT and was stirred for an additional 4 hours. The reaction mixture was directly purified by reverse phase HPLC (acetonitrile/water with 0.1% TFA modifier), and the appropriate fractions were combined and lyophilized to yield the title compound. MS ESI calcd. for $C_{30}H_{33}F_2N_2O_4[M+H]^+$ 523. found 523. $^1$H NMR (500 MHz, $CDCl_3$) δ 8.74 (d, 2.5 Hz, 1H), 7.95 (dd, 2.5 Hz, 8.0 Hz, 1H), 7.84 (d, 8.0 Hz, 1H), 7.74 (dt, 2.0 Hz, 8.0 Hz, 1H), 7.55 (m, 2H), 7.35 (d, 8.0 Hz, 1H), 6.90-6.78 (m, 2H), 4.72 (m, 1H), 2.91-2.78 (m, 2H), 2.76-2.67 (m, 2H), 2.74 (m, 1H), 2.21 (m, 1H), 2.16-2.07 (m, 1H), 2.00 (m, 1H), 1.57 (d, 6.0 Hz, 3H), 1.49 (s, 9H), 1.11 (d, 6.0 Hz, 3H).

Step 2: 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl) acetic acid To a solution of tert-butyl 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)acetate (380 mg, 0.727 mmol) in DCM (6 mL) was added TFA (2 mL, 26.0 mmol) at 0° C. After addition, the reaction was warmed to RT and was stirred for 2 hours. The reaction was concentrated under reduced pressure to yield the title compound, which was carried forward without further purification. MS ESI calcd. for $C_{26}H_{25}F_2N_2O_4[M+H]^+$ 467. found 467. $^1$H NMR (500 MHz, $CD_3OD$) δ 8.74 (d, 2.5 Hz, 1H), 7.95 (dd, 2.5 Hz, 8.0 Hz, 1H), 7.84 (d, 8.0 Hz, 1H), 7.74 (dt, 2.0 Hz, 8.0 Hz, 1H), 7.55 (m, 2H), 7.35 (d, 8.0 Hz, 1H), 6.90-6.78 (m, 2H), 4.72 (m, 1H), 2.91-2.78 (m, 2H), 2.76-2.67 (m, 2H), 2.74 (m, 1H), 2.21 (m, 1H), 2.16-2.07 (m, 1H), 2.00 (m, 1H), 1.57 (d, 6.0 Hz, 3H), 1.49 (s, 9H), 1.11 (d, 6.0 Hz, 3H).

Step 3: 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)acetamide To a solution of 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)acetic acid (100 mg, 0.214 mmol) in $CH_2Cl_2$ (8 mL) was added oxalyl chloride (0.038 mL, 0.429 mmol) at 0° C. After stirring at 0° C. for 30 minutes, the reaction was concentrated under reduced pressure to yield precipitate. After redisolving in $CH_2Cl_2$ (8 mL) and cooling to 0° C., excess aqueous $NH_4OH$ was added. The reaction solution was stirred at 0° C. for 20 minutes, and slowly warmed to room temperature and stirred for 2 more hours. The reaction mixture was concentrated and was directly purified by reverse phase HPLC (acetonitrile/water with 0.1% TFA modifier) to obtain the title compound. MS ESI calcd. for $C_{26}H_{26}F_2N_3O_3[M+H]^+$ 466. found 466. $^1$H NMR (500 MHz, $CD_3OD$) δ 8.85 (d, 2.0 Hz, 1H), 8.32 (dd, 2.0 Hz, 8.5 Hz, 1H), 7.93 (t, 8.5 Hz, 2H), 7.84 (dt, 1.5 Hz, 8.0 Hz, 1H), 7.71 (d, 8.0 Hz, 1H), 7.66 (dt, 1.0 Hz, 8.0 Hz, 1H), 6.90 (dd, 9.5 Hz, 15.5 Hz, 1H), 6.82 (d, 15.5 Hz, 1H), 4.91 (m, 1H), 2.97 (dd, 2.0 Hz, 16.5 Hz, 1H), 2.83 (m, 1H), 2.76 (d, 16.5 Hz, 1H), 2.75 (m, 1H), 2.41-2.33 (m, 1H), 2.22 (dt, 4.0 Hz, 15.0 Hz, 1H), 2.15 (m, 1H), 1.45 (d, 6.0 Hz, 3H), 1.08 (d, 6.0 Hz, 3H). PAR-1 FLIPR $IC_{50}$=3.14 nM.

The following examples in Table 5 were prepared according to Scheme 2 using the procedure outlined in the synthesis of Example 5. Intermediate C or D may be used in step 1. In some cases, chiral separation of products was carried out to yield enantiomerically pure compounds using SFC (IC column, 60%/40% 2:1 MeOH:acetonitrile/$CO_2$).

TABLE 5

| Ex | Structure | IUPAC Name | Exact Mass [M + H]+ | PAR-1 LIPR $IC_{50}$ (nM) |
|---|---|---|---|---|
| 6 | 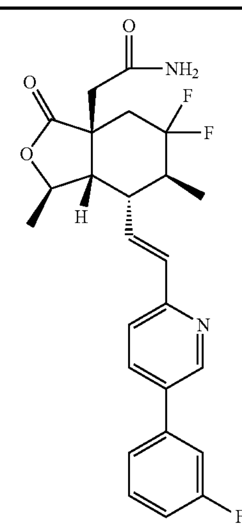 | 2-((1R,3aR, 6S,7R,7aS)-5,5-difluoro-7-((E)-2-(5-(3-fluorophenyl)pyridin-2-yl)vinyl)-1,6-dimethyl-3-oxooctahydroisobenzofuran-3a-yl)acetamide | 459 | 2.62 |

TABLE 5-continued

| Ex | Structure | IUPAC Name | Exact Mass [M + H]+ | PAR-1 LIPR IC$_{50}$ (nM) |
|---|---|---|---|---|
| 7 | 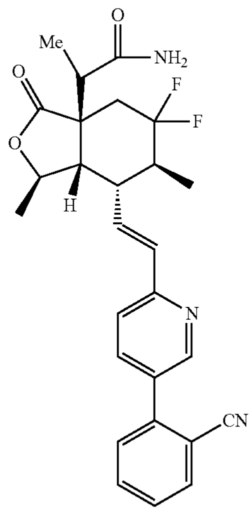 [SMILES: CC(C(N)=O)[C@@]12CC(F)(F)[C@@H](C)[C@H](/C=C/c3ccc(-c4ccccc4C#N)cn3)[C@@H]1[C@@H](C)OC2=O] | 2-((1R,3aR, 6S,7R,7aS)-7-((E)-2-(5-(2-cyanophenyl) pyridin-2-yl)vinyl)-5,5-difluoro-1,6-dimethyl-3-oxooctahydro-isobenzofuran-3a-yl)propanamide | 480 | 4.43 |
| 8 | 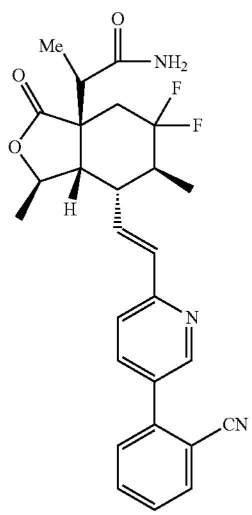 [SMILES: CC(C(N)=O)[C@@]12CC(F)(F)[C@@H](C)[C@H](/C=C/c3ccc(-c4ccccc4C#N)cn3)[C@@H]1[C@@H](C)OC2=O] | (R or S)-2-((1R,3aR,6S,7R,7aS)-7-((E)-2-(5-(2-cyanophenyl) pyridin-2-yl)vinyl)-5,5-difluoro-1,6-dimethyl-3-oxooctahydro-isobenzofuran-3a-yl)propanamide (faster eluting isomer) | 480 | 4.07 |
| 9 | 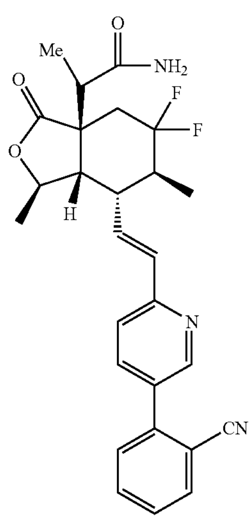 [SMILES: CC(C(N)=O)[C@@]12CC(F)(F)[C@@H](C)[C@H](/C=C/c3ccc(-c4ccccc4C#N)cn3)[C@@H]1[C@@H](C)OC2=O] | (S or R)-2-((1R,3aR,6S,7R,7aS)-7-((E)-2-(5-(2-cyanophenyl) pyridin-2-yl)vinyl)-5,5-difluoro-1,6-dimethyl-3-oxooctahydro-isobenzofuran-3a-yl)propanamide (slower eluting isomer) | 480 | 11.34 |

Example 10

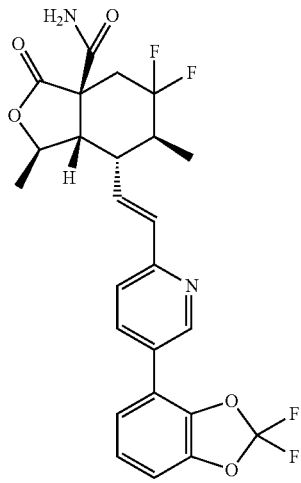 [SMILES: C[C@H]1OC(=O)[C@]2(C(N)=O)CC(F)(F)[C@@H](C)[C@H](/C=C/c3ccc(-c4cccc5c4OC(F)(F)O5)cn3)[C@H]12]

Step 1: (1R,3aR,6S,7R,7aS)-methyl 7-((E)-2-(5-bromopyridin-2-yl)vinyl)-5,5-difluoro-1,6-dimethyl-3-oxooctahydroisobenzofuran-3a-carboxylate To (3R,3aS,4R,5S,7aR)-4-((E)-2-(5-bromopyridin-2-yl) vinyl)-6, 6-difluoro-3, 5-dimethylhexahydroisobenzofuran-1 (3H)-one (3.86 g, 10.0 mmol) in THF (30 mL) at 0° C. under N$_2$(g) was added lithium bis(trimethylsilyl)amide (12.5 mL, 12.5 mmol, 1 M in THF). The reaction mixture was stirred at 0° C. for 30 min before cooling the system to −78° C., and adding methyl cyanoformate (1.11 g, 13.0 mmol). After stirring for 40 min at −78° C., the reaction mixture was allowed to warm to RT and was stirred for 20 min. The reaction mixture was cooled to 0° C., quenched with sat. NH$_4$Cl$_{(aq)}$, and the product was extracted with EtOAc. The organic phase was washed with brine, dried with Na$_2$SO$_4$, and was concentrated. The residue was purified by column chromatography on silica (0-40% EtOAc in hexanes) to afford the title compound. MS ESI calcd. for C$_{19}$H$_{21}$BrF$_2$NO$_4$ [M+H]$^+$ 444/446. found 444/446.

Step 2: (1R,3aR,6S,7R,7aS)-7-((E)-2-(5-bromopyridin-2-yl)vinyl)-5,5-difluoro-1,6-dimethyl-3-oxooctahydroisobenzofuran-3a-carboxylic acid To a solution of (1R,3aR,6S,7R,7aS)-methyl 7-((E)-2-(5-bromopyridin-2-yl)vinyl)-5,5-difluoro-1,6-dimethyl-3-oxooctahydroisobenzofuran-3a-carboxylate in DCM (20 mL), boron tribromide (20 mL, 20 mmol, 1 M in DCM) was added at 0° C. under N$_2$(g). After stirring at 0° C. for 30 min, the reaction mixture was allowed to warm to room RT and stirred for 30 min. Upon completion of the reaction, the system was cooled to 0° C. and was quenched with water. The product was extracted with EtOAc and the organic phase was dried with Na$_2$SO$_4$ before concentrating. The residue was purified by column chromatography on silica (0-10% MeOH in DCM) to provide the title compound. MS ESI calcd. for C$_{18}$H$_{19}$BrF$_2$NO$_4$ [M+H]$^+$ 430/432. found 430/432.

Step 3: (1R,3aR,6S,7R,7aS)-7-((E)-2-(5-bromopyridin-2-yl)vinyl)-5,5-difluoro-1,6-dimethyl-3-oxooctahydroisobenzofuran-3a-carboxamide HATU (494 mg, 1.30 mmol) was added to a solution of (1R,3aR,6S,7R,7aS)-7-((E)-2-(5-bromopyridin-2-yl)vinyl)-5,5-difluoro-1,6-dimethyl-3-oxooctahydroisobenzofuran-3a-carboxylic acid (430 mg, 1.0 mmol) in DMF (5 mL). The solution was stirred at 25° C. for 5 min, before ammonia (6.0 mL, 3.01 mmol, 0.5 M in dioxanes) was added to the reaction mixture. After 1 hour at 25° C., the reaction mixture was diluted with EtOAc and the organic was washed with water and brine. The organic phase was dried with $Na_2SO_4$, concentrated, and was purified by silica gel chromatography (0-50% EtOAc in hexanes) to provide the title compound. MS ESI calcd. for $C_{18}H_{20}BrF_2N_2O_3$ $[M+H]^+$ 429/431. found 429/431.

Step 4: (1R,3aR,6S,7R,7aS)-7-((E)-2-(5-(2,2-difluorobenzo[d][1,3]dioxol-4-yl)pyridin-2-yl)vinyl)-5,5-difluoro-1,6-dimethyl-3-oxooctahydroisobenzofuran-3a-carboxamide To a mixture of (1R,3aR,6S,7R,7aS)-7-((E)-2-(5-bromopyridin-2-yl)vinyl)-5,5-difluoro-1,6-dimethyl-3-oxooctahydroisobenzofuran-3a-carboxamide (0.073 g, 0.170 mmol), 2,2-difluorobenzo [1,3]dioxole-4-boronic acid (0.069 g, 0.34 mmol), and tribasic potassium phosphate (0.25 mL, 0.51 mmol, 2 M in water) in THF (1.0 mL) was added 1,1'-bis(di-tert-butylphosphino)ferrocene palladium dichloride (0.011 g, 0.017 mmol) at RT. The system was purged and flushed with $N_2(g)$ and the reaction mixture was stirred at 50° C. for 2 hours. The reaction mixture was diluted with EtOAc, and the organic was washed with water and brine. The organic phase was dried with $Na_2SO_4$, and was concentrated under reduced pressure. The crude was purified by silica gel chromatography (0-50% EtOAc in hexanes) to provide the title compound. MS ESI calcd. for $C_{25}H_{23}F_4N_2O_3[M+H]^+$ 507. found 507. $^1$H NMR (500 MHz, $CDCl_3$) δ 8.90 (s, 1H); 7.98 (dd, J=8.0, 2.5 Hz, 1H); 7.31 (d, J=7.69, 2 H); 7.22 (t, J=15.1 Hz, 1H); 7.12 (d, J=7.05, 1 H); 7.02 (s, 1H); 6.75 (d, J=15.3 Hz, 1H); 6.67 (t, J=7.8 Hz, 1H); 6.67 to 6.73 (m, 1H); 4.66-4.74 (m, 1H); 4.12 (q, J=7.1 Hz, 1H); 3.13-3.24 (m, 1H); 2.89 (s, 1H); 2.66-2.75 (m, 1H); 2.17-2.31 (m, 1H); 2.04-2.15 (m, 1H); 1.51 (d, J=17 Hz, 3H); 1.09 (d, J=6.5 Hz, 3H). PAR-1 FLIPR $IC_{50}$=4.49 nM.

The following examples in Table 6 were prepared according to Schemes 1 and 3 using the procedure outlined in the synthesis of Example 10 using known or commercially available boronic acids and esters in step 4.

TABLE 6

| Ex | Structure | IUPAC Name | Exact Mass [M + H]+ | PAR-1 FLIPR $IC_{50}$ (nM) |
|---|---|---|---|---|
| 11 | 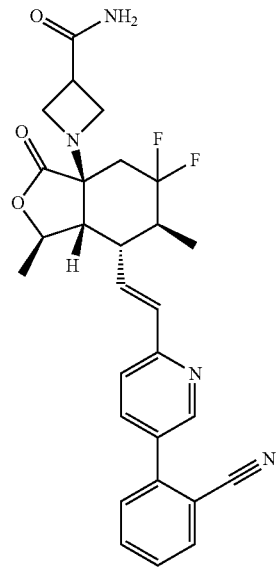 [SMILES: C[C@H]1OC(=O)[C@]2(N3CC(C(N)=O)C3)CC(F)(F)[C@@H](C)[C@H](/C=C/c3ccc(-c4ccccc4C#N)cn3)[C@H]12] | 1R,3aR,6S, 7R,7aS)-7-((E)-2-(2'-cyano-[3,3'-bipyridin]-6-yl)vinyl)-5,5-difluoro-1,6-dimethyl-3-oxooctahydro-isobenzofuran-3a-carboxamide | 453 | 9.68 |

Example 12

1-((1R,3aS,6S,7R,7aS)-7-((E)-2-(5-(2-cyanophenyl) pyridin-2-yl)vinyl)-5, 5-difluoro-1,6-dimethyl-3-oxo-octahydroisobenzofuran-3a-yl)azetidine-3-carboxamide 1-((1R,3aS,6S,7R,7aS)-7-((E)-2-(5-bromopyridin-2-yl) vinyl)-5,5-difluoro-1,6-dimethyl-3-oxo-octahydroisobenzofuran-3a-yl)azetidine-3-carboxamide (8 mg, 0.017 mmol), 2-(5,5-dimethyl-1,3,2-dioxaborinan-2-yl)benzonitrile (5 mg, 0.023 mmol), $K_2CO_3$ (6 mg, 0.043 mmol) and $Pd(PPh_3)_4$ (2 mg, 1.731 mol) were mixed in dioxane (1.5 mL) and water (0.3 mL) in a sealed tube under $N_2$. The mixture was stirred for 1 h at 75° C., and cooled to rt. The reaction mixture was concentrated under reduced pressure and the residue was purified with prep-HPLC (acetonitrile/water with 0.08% NH$_4$HCO$_3$ modifier) to afford the title compound. MS ESI calcd. for C$_{28}$H$_{29}$F$_2$N$_4$O$_3$[M+H]$^+$ 507. found, 507. $^1$H NMR (400 MHz, MeOD) δ 8.73 (d, J=2 Hz, 1H), 8.05 (dd, J=2 Hz, 8.2 Hz, 1H), 7.92 (d, J=8 Hz, 1H), 7.84-7.80 (m, 1H), 7.69-7.61 (m, 3H), 6.80-6.74 (m, 2H), 4.17-4.14 (m, 1H), 4.04-4.01 (m, 1H), 3.57-3.47 (m, 2H), 3.28-3.23 (m, 2H), 2.88-2.82 (m, 1H), 2.40-2.11 (m, 4H), 1.44 (d, J=6 Hz, 3H), 1.08 (d, J=6.4 Hz, 3H). PAR-1 FLIPR IC$_{50}$=5.7 nM.

The following examples in Table 7 were prepared according to Scheme 3 using the procedure outlined in the synthesis of Example 12 using known or commercially available boronic acids and esters.

TABLE 7

| Ex | Structure | IUPAC Name | Exact Mass [M + H]+ | PAR-1 FLIPR IC$_{50}$ (nM) |
|---|---|---|---|---|
| 13 | 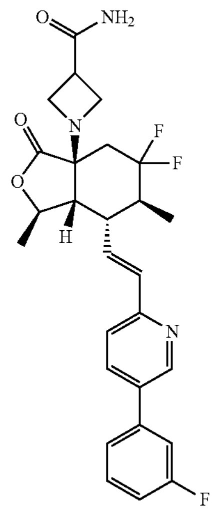 [SMILES: C[C@H]1OC(=O)[C@]2(N3CC(C(N)=O)C3)CC(F)(F)[C@@H](C)[C@H](/C=C/c3ccc(-c4cccc(F)c4)cn3)[C@H]12] | 1-((1R,3aS,6S,7R,7aS)-5,5-difluoro-7-((E)-2-(5-(3-fluorophenyl)pyridin-2-yl)vinyl)-1,6-dimethyl-3-oxo-octahydro-isobenzofuran-3a-yl)azetidine-3-carboxamide | 500 | 13.9 |

Example 14

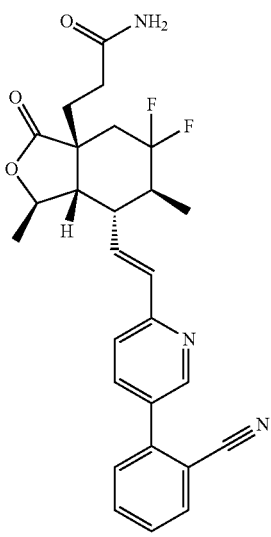 [SMILES: C[C@H]1OC(=O)[C@]2(CCC(N)=O)CC(F)(F)[C@@H](C)[C@H](/C=C/c3ccc(-c4ccccc4C#N)cn3)[C@H]12]

Step 1: tert-butyl 3-((1R,3aR,6S,7R,7aS)-7-((E)-2-(5-bromopyridin-2-yl)vinyl)-5,5-difluoro-1,6-dimethyl-3-oxooctahydroisobenzofuran-3a-yl)propanoate A solution of (3R,3aS,4R,5S,7aR)-4-((E)-2-(5-bromopyridin-2-yl)vinyl)-6,6-difluoro-3,5-dimethylhexahydroisobenzofuran-1(3H)-one (80 mg, 0.207 mmol) in THF (1 mL) was rigorously degassed by bubbling N$_2$ through for 20 min. The system was cooled to at 0° C. and LiHMDS (1M in THF, 249 μL, 0.249 mmol) was added. The mixture was stirred for 20 minutes at 0° C., and then cooled to −78° C. before adding tert-butyl 3-bromopropionate (104 μL, 0.621 mmol). The reaction mixture was stirred for 30 min and was allowed to slowly warm to rt. The reaction was diluted with saturated aq. NH$_4$Cl and extracted with EtOAc, dried over anhydrous Na$_2$SO$_4$, and purified by silica gel chromatography (0.25% EtOAc/hexanes) to yield the title compound. MS ESI calcd. for C$_{24}$H$_{31}$BrF$_2$NO$_4$ [M+H]$^+$ 514/516. found 514/516.

Step 2: 3-((1R,3aR,6S,7R,7aS)-7-((E)-2-(5-bromopyridin-2-yl)vinyl)-5,5-difluoro-1,6-dimethyl-3-oxooctahydroisobenzofuran-3a-yl)propanoic acid To a solution of tert-butyl 3-((1R,3aR,6S,7R,7aS)-7-((E)-2-(5-bromopyridin-2-yl)vinyl)-5,5-difluoro-1,6-dimethyl-3-oxooctahydroisobenzofuran-3a-yl)propanoate (54 mg, 0.105 mmol) in DCM (1 mL), cooled to 0° C. was added TFA (300 μL, 3.89 mmol). The reaction was allowed to warm to rt and was stirred for 3 h. The volatiles were removed under reduced pressure and the residue was diluted with DCM and poured into saturated aq. NaHCO$_3$. The organic was washed with brine, dried over anhydrous Na$_2$SO$_4$, filtered and concentrated. The title compound was carried forward without further purification. MS ESI calcd. for C$_{20}$H$_{23}$BrF$_2$NO$_4$ [M+H]$^+$ 458/460. found 458/460.

Step 3: 3-((1R,3aR,6S,7R,7aS)-7-((E)-2-(5-bromopyridin-2-yl)vinyl)-5,5-difluoro-1,6-dimethyl-3-oxooctahydroisobenzofuran-3a-yl)propanamide A solution of 3-((1R,3aR,6S,7R,7aS)-7-((E)-2-(5-bromopyridin-2-yl)vinyl)-5,5-difluoro-1,6-dimethyl-3-oxooctahydroisobenzofuran-3a-yl)propanoic acid (48 mg, 0.105 mmol), HATU (49.8 mg, 0.131 mmol) and TEA (21.90 μL, 0.157 mmol) in DMF (1 mL) was stirred at rt for 5 min. Ammonia (419 μL, 0.209 mmol) was added to the reaction mixture and the reaction mixture was stirred at rt for 1 h. The reaction mixture was poured into water and EtOAc. The organic was washed with brine, dried over anhydrous Na$_2$SO$_4$, concentrated and purified by silica gel chromatography (30-80% EtOAc in hexanes) to provide the title compound. MS ESI calcd. for C$_{20}$H$_{24}$BrF$_2$N$_2$O$_3$ [M+H]$^+$ 457/459. found 457/459.

Step 4: 3-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)propanamide To 3-((1R,3aR,6S,7R,7aS)-7-((E)-2-(5-bromopyridin-2-yl)vinyl)-5,5-difluoro-1,6-dimethyl-3-oxooctahydroisobenzofuran-3a-yl)propanamide (39 mg, 0.085 mmol) in a microwave vial was added THF (1 mL), (2-cyanophenyl)boronic acid (25.1 mg, 0.171 mmol) and aq. K$_2$CO$_3$ (2 M, 128 μL, 0.256 mmol). The system was purged and flushed with N$_2$ (3 times) before adding 1,1'-bis(di-tert-butylphosphino)ferrocene palladium dichloride (2.78 mg, 4.26 mol). The system was purged and flushed with N$_2$ (3 times) before sealing the system and heating to 40° C. After 2.5 h the reaction was cooled to rt, diluted with water and extracted with EtOAc. The organic layer was washed with brine, dried over anhydrous sodium sulfate, filtered and concentrated to dryness before purification by reverse phase chromatography (acetonitrile/water with 0.05% TFA modifier) to yield the title compound. MS ESI calcd. for $C_{27}H_{28}F_2N_3O_3$[M+H]$^+$ 480. found 480. $^1$H NMR (400 MHz, MeOD) δ 1.08 (3H, d, J=6.62 Hz), 1.44 (3H, d, J=5.90 Hz), 2.03-1.96 (1H, m), 2.42-2.13 (7H, m), 2.92-2.85 (1H, m), 4.95-4.89 (1H, m), 6.85 (2H, d, J=3.95 Hz), 7.71-7.63 (2H, m), 7.84-7.81 (2H, m), 7.93 (1H, d, J=7.84 Hz), 8.23 (1H, d, J=8.06 Hz), 8.81 (1H, s). PAR-1 FLIPR IC$_{50}$=4.4 nM.

The following examples in Table 8 were prepared according to Schemes 2 and 3 using the procedure outlined in the synthesis of Example 14 using known or commercially available boronic acids and esters in step 4.

TABLE 8

| Ex | Structure | IUPAC Name | Exact Mass [M + H]+ | PAR-1 FLIPR IC$_{50}$ (nM) |
|---|---|---|---|---|
| 15 | 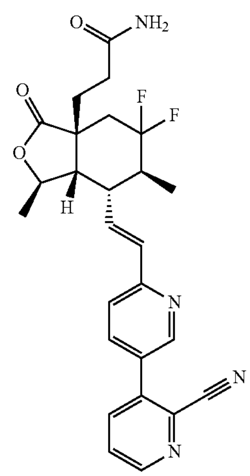 [SMILES: C[C@H]1OC(=O)[C@]2(CCC(N)=O)CC(F)(F)[C@@H](C)[C@H](/C=C/c3ccc(-c4cccnc4C#N)cn3)[C@H]12] | 3-((1R,3aR,6S,7R,7aS)-7-((E)-2-(2'-cyano-[3,3'-bipyridin]-6-yl)vinyl)-5,5-difluoro-1,6-dimethyl-3-oxooctahydro-isobenzofuran-3a-yl)propanamide | 481 | 6.34 |
| 16 | 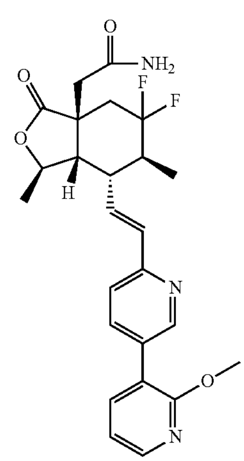 [SMILES: COc1ncccc1-c1ccc(/C=C/[C@@H]2[C@@H]3[C@@H](C)OC(=O)[C@]3(CC(N)=O)CC(F)(F)[C@H]2C)nc1] | 2-((1R,3aR,6S,7R,7aS)-5,5-difluoro-7-((E)-2-(2'-methoxy-[3,3'-bipyridin]-6-yl)vinyl)-1,6-dimethyl-3-oxooctahydro-isobenzofuran-3a-yl)acetamide | 472 | 103.7 |
| 17 | | 2-((1R,3aR,6S,7R,7aS)-7-((E)-2-(2'-cyano-[3,3'-bipyridin]-6-yl)vinyl)-5,5-difluoro-1,6-dimethyl-3-oxooctahydro-isobenzofuran-3a-yl)acetamide | 467 | 21.2 |

Example 18

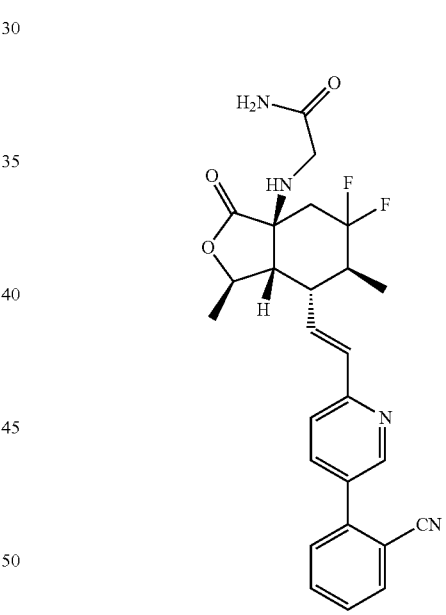

Step 1: 2-(6-((E)-2-((3R,3aS,4R,5S,7aS)-7a-azido-6,6-difluoro-3,5-dimethyl-1-oxooctahydroisobenzofuran-4-yl)vinyl)pyridin-3-yl)benzonitrile To a solution of 2-(6-((E)-2-((3R,3aS,4R,5S,7aR)-6,6-difluoro-3,5-dimethyl-1-oxooctahydroisobenzofuran-4-yl)vinyl)pyridin-3-yl)benzonitrile (0.904 g, 2.2 mmol) in THF (12 mL) was added KHMDS (1 M in THF, 2.8 mL, 2.8 mmol) at 0° C. The resulting mixture was stirred at 0° C. for 15 minutes before cooling down to −78° C. A cooled solution (cooled at 0° C.) of 2,4,6-triisopropylbenzenesulfonyl azide (1.0 g, 3.3 mmol) was added and stirred for 3 minutes, then acetic acid was added (0.38 mL, 6.6 mmol).

The dry ice bath was replaced with the warm water bath and the reaction mixture was stirred for 1 h, and then was transferred to a sepatory funnel, whereupon was added 50 mL of water and was neutralized using saturated aq. NaHCO$_3$ to pH 7.0. The resulting solution was extracted using dichloromethane (3×100 mL), the organic layer was dried over anhydrous MgSO$_4$, concentrated and purified by silica gel chromatography (0-100% ethyl acetate in hexanes) to provide the title compound.

Step 2: 2-(6-((E)-2-((3R,3aS,4R,5S,7aS)-7a-amino-6,6-difluoro-3,5-dimethyl-1-oxooctahydroisobenzofuran-4-yl)vinyl)pyridin-3-yl)benzonitrile To a solution of 2-(6-((E)-2-((3R,3aS,4R,5S,7aS)-7a-azido-6,6-difluoro-3,5-dimethyl-1-oxooctahydroisobenzofuran-4-yl)vinyl)pyridin-3-yl)benzonitrile obtained above (600 mg, 1.41 mmol) in the mixture ethyl acetate and water (6.5 mL ethyl acetate and 1 mL water) was added 1 M solution of PMe$_3$ (2.1 mmol, 2.1 mL) and the resulting solution was stirred for 2 h, then was transferred to a separatory funnel. The resulting solution was extracted using dichloromethane (3×100 mL), the organic layer was dried over anhydrous MgSO$_4$, and the solvent was removed under reduced pressure. The crude product was purified by silica gel chromatography (0-100% ethyl acetate in hexanes) to provide the title compound. $^1$H NMR δ 8.71 (m, 1H), 7.89 (m, 1H), 7.80 (m, 1H), 7.71 (m, 1H), 7.53 (m, 2H), 7.32 (m, 1H), 6.65 (m, 2H), 4.63 (m, 1H), 2.88 (m, 1H), 2.2 (m, 2H), 2.21-1.98 (m, 2H), 1.74 (br-s, 2H), 1.81 (d, J=8 Hz, 3H), 1.10 (d, J=10 Hz, 3H).

Step 3: ethyl 2-(((1R,3aS,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)amino) acetate To a solution of 2-(6-((E)-2-((3R,3aS,4R,5S,7aS)-7a-amino-6,6-difluoro-3,5-dimethyl-1-oxooctahydroisobenzofuran-4-yl)vinyl)pyridin-3-yl)benzonitrile (54 mg, 0.128 mmol) and ethyl glyoxalate (156 mg, 50 wt %, 0.765 mmol) were combined in MeOH (1.0 mL). Glacial acetic acid (22 µL, 0.38 mmol) was added and the reaction was stirred for 20 min at rt. Then sodium cyanoborohydride (10.4 mg, 0.166 mmol) was added and the pH was checked again to ensure it was ~pH=5. After 1 hour, the reaction was poured into saturated aq. NaHCO$_3$ (1 mL) and extracted into DCM (2×3 mL). The organics were dried (anhydrous Na$_2$SO$_4$), filtered and concentrated before purification by chromatography on silica (0-45% EtOAc/hexanes) to yield the title compound. MS ESI calcd. for C$_{28}$H$_{30}$F$_2$N$_3$O$_4$[M+H]$^+$ 510. found 510.

Step 4: 2-(((1R,3aS,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)amino) acetic acid To a solution of ethyl 2-(((1R,3aS,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)amino) acetate (45 mg, 0.088 mmol) in THF (662 µL) and water (0.1 mL) was added aq. LiOH (1 M, 106 µL, 0.106 mmol). After 6 hr, the reaction was acidified with TFA. The volatiles were removed under reduced pressure and the residue was dissolved in EtOAc and washed with saturated aq. NaHCO$_3$, brine, dried over anhydrous Na$_2$SO$_4$, filtered, and concentrated. The title compound was carried forward without further purification.

Step 5: 2-(((1R,3aS,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)amino) acetamide To a solution of 2-(((1R,3aS,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)amino)acetic acid (30 mg, 0.062 mmol), HATU (29.6 mg, 0.078 mmol) and TEA (13.03 µL, 0.093 mmol) in DMF (1 mL) was added ammonia (249 µL, 0.125 mmol). The reaction mixture was stirred at rt for 1 h. and was diluted with EtOAc. The organic phase was washed with water and brine, dried with anhydrous Na$_2$SO$_4$, concentrated and purified HPLC (acetonitrile/water with 0.05% TFA) to yield the title compound. MS ESI calcd. for C$_{26}$H$_{27}$F$_2$N$_4$O$_3$[M+H]$^+$ 481. found 481. $^1$H NMR (400 MHz, MeOD) δ 1.13 (3H, d, J=6.60 Hz), 1.50 (3H, d, J=5.92 Hz), 2.50-2.39 (5H, m), 3.06-3.01 (1H, m), 3.55 (2H, s), 5.00-4.87 (1H, m), 6.82-6.81 (2H, m), 7.76-7.63 (3H, m), 7.84 (1H, td, J=7.70, 1.30 Hz), 7.94 (1H, d, J=7.86 Hz), 8.16 (1H, dd, J=8.20, 2.36 Hz), 8.79 (1H, d, J=2.31 Hz). PAR-1 FLIPR IC$_{50}$=4.3 nM.

Example 19

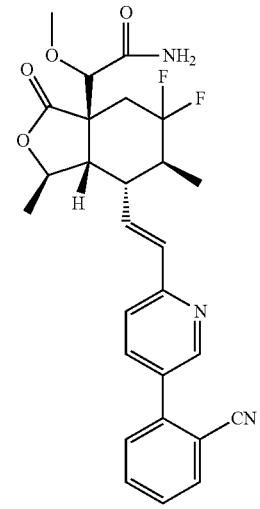 [SMILES: COC(C(N)=O)[C@@]12CC(F)(F)[C@@H](C)[C@H](/C=C/c3ccc(-c4ccccc4C#N)cn3)[C@@H]1[C@@H](C)OC2=O]

Step 1: (S and R)-methyl 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-hydroxyacetate To a solution of 2-(6-((E)-2-((3R,3aS,4R,5S,7aR)-6,6-difluoro-3,5-dimethyl-1-oxooctahydroisobenzofuran-4-yl)vinyl)pyridin-3-yl)benzonitrile (1.0 g, 2.448 mmol) in THF (150 mL) was added lithium bis(trimethylsilyl)amide (1 M in THF, 4.90 mL, 4.90 mmol) at 0° C. After stirring for 30 minutes, methyl glyoxalate (647 mg, 7.35 mmol) was added. The reaction was stirred at 0° C. for 30 minutes, and slowly warmed to room temperature, and stirred for an additional 2 hours. The reaction was diluted with DCM and saturated aq. NH$_4$Cl solution. The organic layer was concentrated and purified on a silica gel column (80% EtOAc in hexanes) to afford the title compound. MS ESI calcd. for C₂₇H₂₇F₂N₂O₅ [M+H]⁺ 497. found 497.

Step 2: (S and R)-methyl 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methoxyacetate To a solution of (S and R)-methyl 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-hydroxyacetate (1.8 g, 3.63 mmol) in methanol (2 mL) was added lithium bis(trimethylsilyl)amide (1 M in THF, 7.25 mL, 7.25 mmol) and iododmethane (0.68 mL, 10.9 mmol) at 0° C. The reaction was stirred at 0° C. for 30 minutes, and slowly warmed to room temperature, and stirred for 24 hours. Volatiles were removed and the residue was purified by HPLC (acetonitrile/water with 0.1% TFA modifier) to yield the title compound. MS ESI calcd. for C₂₈H₂₉F₂N₂O₅[M+H]⁺ 511. found 511.

Step 3: (S and R)-2-((1R,3aR,6S,7R,7aS)-7-((E)-2-(5-(2-carbamoylphenyl)pyridin-2-yl)vinyl)-5,5-difluoro-1,6-dimethyl-3-oxooctahydroisobenzofuran-3a-yl)-2-methoxyacetic acid To a solution of (S and R)-methyl 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methoxyacetate (1.25 g, 2.448 mmol) in dioxane (10 mL) was added lithium hydroxide (0.176 g, 7.35 mmol) in water (5 mL), at 0° C. The reaction was stirred for 30 min before slowly warming to room temperature. After 24 h, volatiles were removed and the residue was purified by silica gel chromatography (20% MeOH in DCM) to afford the title compound. MS ESI calcd. for C₂₇H₂₉F₂N₂O₆[M+H]⁺ 515. found 515.

Step 4: (S and R)-2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methoxyacetamide A solution of (S and R)-methyl 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methoxyacetate (0.85 g, 1.665 mmol) in ammonia (8.32 mL, 16.65 mmol) was stirred in a sealed tube at 50° C. for 2 days. The reaction was concentrated and directly purified by a silica gel chromatography (70% EtOAc in haxanes) to yield the title compound. MS ESI calcd. for C₂₇H₂₈F₂N₃O₄[M+H]⁺ 496. found 496. PAR-1 FLIPR IC₅₀=3.02 mn The following examples in Table 9 were prepared according to Scheme 5 using the procedure outlined in the synthesis of Example 19. In some cases, step 2 may be omitted.

TABLE 9

| Ex | Structure | IUPAC Name | Exact Mass [M + H]+ | PAR-1 FLIPR IC₅₀ (nM) |
|---|---|---|---|---|
| 20 | 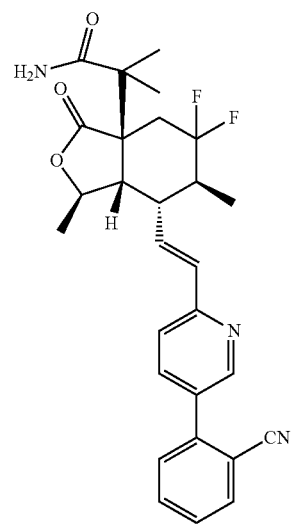 [SMILES: C[C@H]1OC(=O)[C@]2(C(C)(C)C(N)=O)CC(F)(F)[C@@H](C)[C@H](/C=C/c3ccc(-c4ccccc4C#N)cn3)[C@H]12] | (S and R)-2-((1R,3aR,6S,7R,7aS)-7-((E)-2-(5-(2-cyanophenyl)pyridin-2-yl)vinyl)-5,5-difluoro-1,6-dimethyl-3-oxooctahydro-isobenzofuran-3a-yl)-2-hydroxyacetamide | 482 | 4.41 |

Example 21

Step 1: tert-butyl 2-((1R,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methylpropanoate To a solution of (S and R)-tert-butyl 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl) propanoate in THF (150 mL) was added lithium bis(trimethylsilyl)amide (1 M in THF, 1.08 mL, 1.08 mmol) at 0° C. After stirring for 30 minutes, iodomethane (0.10 mL, 1.62 mmol) was added. The reaction was stirred at 0° C. for 30 minutes, and slowly warmed to room temperature. After stirring for 2 h, the reaction was diluted with saturated aq.

NH$_4$Cl, and extracted with EtOAc. The organic layer was concentrated and purified by silica gel chromatography (40% EtOAc in hexanes) to afford the title compound. MS ESI calcd. for C$_{32}$H$_{37}$F$_2$N$_2$O$_4$[M+H]$^+$ 551. found 551. $^1$H NMR (CDCl$_3$, 500 mHz): 9.05 (s, 1H), 8.46 (dd, 2.0 Hz, 8.0 Hz, 1H), 7.92 (d, 7.5 Hz, 1H), 7.86-7.82 (m, 2H), 7.68 (m, 2H), 6.85 (m, 2H), 4.58 (m, 1H), 2.71 (m, 1H), 2.63 (m, 1H), 2.50 (m, 1H), 2.47-2.35 (m, 2H), 1.55 (m, 9H), 1.47 (d, 2.0H, 3H), 1.34 (s, 3H), 1.30 (s, 3H), 1.15 (m, 3H).

Step 2: 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methylpropanoic acid To a solution of tert-butyl 2-((1R,3aR,6S,7R,7aS)-7-((E)-2-(5-(2-cyanophenyl)pyridin-2-yl)vinyl)-5, 5-difluoro-1,6-dimethyl-3-oxooctahydroisobenzofuran-3a-yl)-2-methylpropanoate (220 mg, 0.40 mmol) in DCM (5 mL) was added TFA (2 mL, 26.0 mmol) at 0° C. After stirring for 2 h, the volatiles were removed and the title compound was carried forward without purification. MS ESI calcd. for C$_{28}$H$_{29}$F$_2$N$_2$O$_4$[M+H]$^+$ 495. found 495.

Step 3: 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methylpropanamide To a solution of 2-((1R,3aR,6S,7R,7aS)-7-((E)-2-(5-(2-cyanophenyl)pyridin-2-yl)vinyl)-5,5-difluoro-1, 6-dimethyl-3-oxooctahydroisobenzofuran-3a-yl)-2-methylpropanoic acid (200 mg, 0.404 mmol) in DCM (3 mL) was added oxalyl chloride (0.404 mL, 0.809 mmol) at 0° C. After stirring at 0° C. for 30 minutes, it was concentrated and azotroped with toluene. This resultant solid was redissolved in 40 mL of DCM, and cooled to 0° C., before an excess of aq. NH$_4$OH was added. The reaction solution was stirred at 0° C. for 30 minutes before it was concentrated and filtered through celite to yield the title compound. MS ESI calcd. for C$_{28}$H$_{30}$F$_2$N$_3$O$_3$[M+H]$^+$ 494. found 494. $^1$H NMR (CDCl$_3$, 500 mHz): 8.91 (s, 1H), 8.27 (d, 8.0 Hz, 1H), 7.89 (d, 8.0 Hz, 1H), 7.79 (m, 1H), 7.70 (d, 8.0 Hz, 1H), 7.62 (m, 2 HH), 6.90-6.77 (m, 2H), 6.02 (broad s, 1H), 5.77 (broad s, 1H), 4.58 (m, 1H), 2.68 (m, 1H), 2.60 (m, 1H), 2.45-2.35 (m, 2H), 1.45 (s, 3H), 1.43 (d, 6.0 Hz, 3H), 1.41 (s, 3H), 1.11 (m, 3H). PAR-1 FLIPR IC$_{50}$=17.1 nM.

Assays

The following assays were used to evaluate the ability of the inventive compounds to act as PAR-1 receptor antagonists and their inability to cause drug-induced long QT syndrome.

PAR-1 FLIPR Assay

This assay measures the potency of the inventive compounds as PAR-1 receptor antagonists.

Frozen HEK 293 Cells were plated in 384-well PDL coated plates at 12000 cells/well in 50 uL of DMEM media containing 10% FBS, pen/strep/L-Glutamine and non-essential amino acids, incubated overnight at 37° C./5% CO$_2$. Media was then removed from the cells, incubated with 33 ul of Calcium-5 dye in assay buffer (Hank's buffer containing 20 mM HEPES, 0.04% Chaps and 2.5 mM Probenecid) for 60 minutes at 37° C. 2 uL of varying concentrations of compound in 40% DMSO in assay buffer (final DMSO concentration is 2.3%) were then added to the cells and incubated at 25° C. for 30 minutes. The plates were added to the FLIPR Tetra, the device added 5 uL of PAR-1 selective receptor-activating peptide (sequence Ala-parafluoroPhe-Arg-Cha-Cit-Try-NH$_2$, prepared in water) at a concentration equal to the effective concentration that achieved 80% activation of signaling on the day of the experiment. The range of peptide was from 1.5-3 μM. The final volume was 40 uL/well, with 2% DMSO. The FLIPR was read at an excitation wavelength of 480 nm and an emission wavelength of 535 nm, and performed 60 scans over a 1-2 min reading time. The data were analyzed by taking the peak signal over a portion of the range of the 60 scans and dividing this signal by the minimum signal for that same range. The data were expressed as percent inhibition of the maximum divided by the minimum signal achieved at 80% activation produced by the PAR-1 activating peptide on the test day. The compounds of Examples 1-21 were tested in the assay described above and the data collected for these compounds is provided.

MK-499 Filter Binding Assay

This assay is used to evaluate the potential of a compound to cause drug-induced long QT syndrome.

Drug cardiac arrhythmia is an important safety concern for pharmaceutical development and health regulatory authorities. Blockade of heterologously-expressed human ether-a-go-go gene (hERG) channel prolongs the duration of the cardiac action potential leading to a long QT interval that can lead to sudden death (De Ponti, F.; et al Drug Safety 2002, 25, pp. 263-286). It is important to have compounds devoid of hERG channel activity as measured by an in vitro assay. Affinity of compounds for the hERG channel was evaluated in radioligand competition experiments using HEK293 cells that were stably transfected with the hERG channel and radiolabeled ligand, MK-499 a potent antiarrhythmic. This assay correlates well with QT prolongation in vivo (Jamieson, C.; et al., *J. Med. Chem.* 2006, 49, pp. 5029-5046).

25 μL Target membranes (in assay buffer: 10 mM HEPES/NaOH, pH 7.4, 70 mM NaCl, 60 mM KCl, 2 mM MgCl2, 1 mM CaCl$_2$) purified from a HEK293 cell line expressing the human Ether-á-go-go Related Gene (hERG) ion channel, 1 μL test compound in 10 mM DMSO and 25 μL (6,000 cpm/well; in assay buffer) [35S]MK-0499 radioligand (Merck/Perkin Elmer) were added to the assay plate (Axygen; 384 Deep well "Diamond Plate", clear). After incubation of the binding reaction at room temperature (RT) for 90 min 50 μL of the assay were transferred to a Multiscreen HTS 384 FC filter plate (Millipore), which had been pre-wetted with 20 μL 0.01% PEI/0.01% Triton X-100 for at least 30 min at RT. Then, 30 μL wash buffer (10 mM HEPES/NaOH, pH 7.4, 130 mM NaCl, 2 mM MgCl$_2$, 1 mM CaCl$_2$) equilibrated to RT were added to each well of the assay plate and subsequently transferred to the filter plate. The assay mixture was aspirated through the filter plate using a Biotek ELx405™ washer. The filter plate was washed twice with 100 μl cold wash buffer per wash and well and then dried in a drying oven for at least 75 min at 55° C. Afterwards, the bottom of each filter plate was heat sealed with a solid foil seal, then 10 μL of Microscint™ 0 (Perkin Elmer) were added to each well of the filter plate and finally, the top of each filter plate was sealed with a clear seal. The plates were stored for at least 20 min in a MicroBeta2 reader (Perkin Elmer) before they are counted (60 sec/well).

Table 10 summarizes the ability of the inventive compound to inhibit hERG activity.

TABLE 10

| Ex | MK499 IC$_{50}$ (µM) |
|---|---|
| 1 | 43.9 |
| 2 | 13.0 |
| 3 | 12.0 |
| 4 | 60 |
| 5 | 60 |
| 6 | 20.4 |
| 7 | 39.1 |
| 8 | 26.3 |
| 9 | 59.7 |
| 10 | 15.4 |
| 11 | 60.0 |
| 12 | 16.3 |
| 13 | 3.0 |
| 14 | 14.4 |
| 15 | 60.0 |
| 16 | 25.9 |
| 17 | 21.9 |
| 18 | 46.8 |
| 19 | 47.7 |
| 20 | 60 |
| 21 | 23.4 |

A comparison of the PAR-1 FLIPR assay and the MK-499 Filter Binding assay indicate that the inventive compounds possess good potency and a reduce ability to cause drug-induced log QT syndrome.

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

We claim:

1. A compound of the formula:

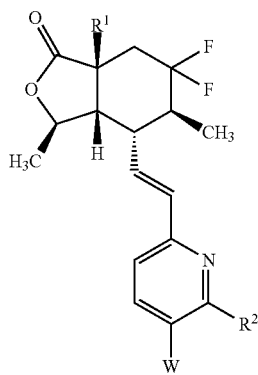

I or a pharmaceutically acceptable salt thereof, wherein:
R$^1$ is —[C(R$^a$)(R$^b$)]$_x$—[C(R$^b$)(R$^b$)]$_y$—C(O)NH$_2$, or —N(H)—[(CH$_2$)]$_z$ C(O)—NH$_2$,
where:
R$^a$ is independently H, —OH or —C$_1$-C$_3$-alkoxy,
R$^b$ is independently H or —C$_1$-C$_3$-alkyl;
R$^2$ is H or alkyl;

W is

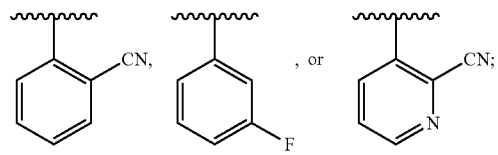

x is 0 or 1;
y is 0, 1, 2 or 3; and
z is 1 or 2
provided that when R$^a$ is OH or —C$_1$-C$_3$-alkoxy, x is 1.

2. A compound as defined in claim 1 or a pharmaceutically acceptable salt thereof wherein
R$^1$ is —(CH$_2$)$_a$—C(O)—NH$_2$, —(NH)—[CH$_2$]$_z$—C(O)—NH$_2$, —CH(CH$_3$)—C(O)—NH$_2$, —C(CH$_3$)(CH$_3$)—C(O)—NH$_2$, —CH(OH)—C(O)—NH$_2$, —CH(OCH$_3$)—C(O)—NH$_2$;
a is 0 or 1; and
z is 1 or 2.

3. The compound of claim 1 or a pharmaceutically acceptable salt thereof which is:
(1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-carboxamide;
(1R,3aR,6S,7R,7aS)-7-((E)-2-(5-(2-cyanophenyl)-6-methylpyridin-2-yl)vinyl)-5,5-difluoro-1,6-dimethyl-3-oxooctahydroisobenzofuran-3a-carboxamide;
2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)acetamide;
2-((1R,3aR,6S,7R,7aS)-5,5-difluoro-7-((E)-2-(5-(3-fluorophenyl)pyridin-2-yl)vinyl)-1,6-dimethyl-3-oxooctahydroisobenzofuran-3a-yl)acetamide;
2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)propanamide;
R or S)-2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)propanamide;
(S or R)-2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)propanamide;
1R,3aR,6S,7R,7aS)-7-((E)-2-(2'-cyano-[3,3'-bipyridin]-6-yl)vinyl)-5,5-difluoro-1,6-dimethyl-3-oxooctahydroisobenzofuran-3a-carboxamide;
3-((1R,3aR,6S,7R,7aS)-7-((E)-2-(2'-cyano-[3,3'-bipyridin]-6-yl)vinyl)-5,5-difluoro-1,6-dimethyl 3-oxooctahydroisobenzofuran-3a-yl) propanamide;
2-((1R,3aR,6S,7R,7aS)-7-((E)-2-(2'-cyano-[3,3'-bipyridin]-6-yl)vinyl)-5,5-difluoro-1,6-dimethyl-3-oxooctahydroisobenzofuran-3a-yl)acetamide;
2-(((1R,3aS,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)amino)acetamide;
(S and R)-2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methoxyacetamide;
(S and R)-2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-hydroxyacetamide; or 2-((1R,3aR,6S,7R,7aS)-7-((E)-2-(5-(2-cyanophenyl)pyridin-2-yl)vinyl)-5,5-difluoro-1,6-dimethyl-3-oxooctahydroisobenzofuran-3a-yl)-2-methylpropanamide.

4. A pharmaceutical composition comprising an effective amount of a compound as defined in claim 1 or a pharmaceutically acceptable salt thereof and a pharmaceutically acceptable carrier.

5. The pharmaceutical composition as defined in claim 4, which further comprises a therapeutically effective amount of at least one additional cardiovascular agent.

6. The pharmaceutical composition as defined in claim 5, wherein the at least one additional cardiovascular agent is aspirin or clopidogrel, wherein clopidogrel is a free base or pharmaceutically acceptable salt.

7. A pharmaceutical composition comprising an effective amount of a compound as defined in claim 3 or a pharmaceutically acceptable salt thereof and a pharmaceutically acceptable carrier.

8. The pharmaceutical composition as defined in claim 7, which further comprises a therapeutically effective amount of at least one additional cardiovascular agent.

9. The pharmaceutical composition as defined in claim 8, wherein the at least one additional cardiovascular agent is aspirin or clopidogrel, wherein clopidogrel is a free base or pharmaceutically acceptable salt.

10. A method for treating acute coronary syndrome or peripheral artery disease by administering a compound as defined in claim 1
or a pharmaceutically acceptable salt thereof
to a mammal in need of such treatment.

11. A method of inhibiting platelet aggregation comprising administering to a mammal an effective amount of a compound as defined in claim 1
or a pharmaceutically acceptable salt thereof.

12. A method for treating acute coronary syndrome or stroke or peripheral artery disease by administering a compound as defined in claim 3 to a mammal in need of such treatment.

13. A method of inhibiting platelet aggregation comprising administering to a mammal an effective amount of a compound as defined in claim 3.

* * * * *